(12) United States Patent  
Katrana et al.

(10) Patent No.: US 9,034,050 B2  
(45) Date of Patent: May 19, 2015

(54) ELBOW PROSTHESIS

(75) Inventors: Nicholas J. Katrana, Fort Wayne, IN (US); Thomas J. Graham, Novelty, OH (US); Brian K. Berelsman, Warsaw, IN (US); Clinton E. Kehres, Pierceton, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 743 days.

(21) Appl. No.: 13/051,559

(22) Filed: Mar. 18, 2011

(65) Prior Publication Data

US 2011/0172781 A1 Jul. 14, 2011

Related U.S. Application Data

(63) Continuation-in-part of application No. 12/562,616, filed on Sep. 18, 2009.

(51) Int. Cl.
*A61F 2/38* (2006.01)
*A61F 2/30* (2006.01)

(52) U.S. Cl.
CPC ............ *A61F 2/3804* (2013.01); *A61F 2/30767* (2013.01); *A61F 2002/30507* (2013.01); *A61F 2002/30594* (2013.01); *A61F 2002/30616* (2013.01); *A61F 2002/3809* (2013.01); *A61F 2002/3813* (2013.01); *A61F 2220/0025* (2013.01)

(58) Field of Classification Search
USPC ........................................... 623/20.11–20.13
See application file for complete search history.

(56) References Cited

U.S. PATENT DOCUMENTS

| | | |
|---|---|---|
| 3,547,115 A | 12/1970 | Stevens |
| 3,694,821 A | 10/1972 | Moritz |
| 3,708,805 A | 1/1973 | Scales et al. |
| 3,816,854 A | 6/1974 | Schlein |
| 3,824,630 A | 7/1974 | Johnston |
| 3,852,831 A | 12/1974 | Dee |
| 3,919,725 A | 11/1975 | Swanson et al. |
| 3,939,496 A | 2/1976 | Ling et al. |
| 3,946,445 A | 3/1976 | Bentley et al. |

(Continued)

FOREIGN PATENT DOCUMENTS

| | | |
|---|---|---|
| DE | 2806717 | 8/1979 |
| DE | 3417923 A1 | 11/1985 |

(Continued)

OTHER PUBLICATIONS

Final Office Action for U.S. Appl. No. 11/384,943 Mailed Dec. 12, 2011.

(Continued)

*Primary Examiner* — Elizabeth Houston
*Assistant Examiner* — Joshua Levine
(74) *Attorney, Agent, or Firm* — Harness, Dickey

(57) ABSTRACT

An elbow prosthesis can include a capitellar implant that has an articulating head and a stem. The articulating head can have a first substantially hemispherical portion and a second portion that collectively extend between lateral and medial sides of the articulating head and are separated by a plane. The first and second portions can generally extend between the lateral and medial sides. The second portion can generally have an attachment lobe that extends on the lateral side and that defines a passage therethrough. The passage can extend at least partially on the second portion.

4 Claims, 23 Drawing Sheets

(56) References Cited

U.S. PATENT DOCUMENTS

| | | | |
|---|---|---|---|
| 3,990,117 A | 11/1976 | Pritchard et al. | |
| 4,001,603 A | 1/1977 | Wilcox | |
| 4,008,495 A | 2/1977 | Cavendish et al. | |
| 4,038,704 A | 8/1977 | Ring et al. | |
| 4,079,469 A | 3/1978 | Wadsworth et al. | |
| 4,129,902 A | 12/1978 | Harmon | |
| 4,131,956 A | 1/1979 | Treace | |
| 4,131,957 A | 1/1979 | Bokros | |
| 4,194,250 A | 3/1980 | Walker | |
| 4,206,516 A | 6/1980 | Pilliar | |
| 4,224,695 A | 9/1980 | Grundei et al. | |
| 4,224,697 A | 9/1980 | Murray et al. | |
| 4,242,758 A | 1/1981 | Amis et al. | |
| 4,259,752 A | 4/1981 | Taleisnik | |
| 4,280,231 A | 7/1981 | Swanson | |
| 4,293,963 A | 10/1981 | Gold et al. | |
| 4,301,552 A | 11/1981 | London | |
| 4,352,212 A | 10/1982 | Greene et al. | |
| 4,378,607 A | 4/1983 | Wadsworth et al. | |
| 4,383,337 A | 5/1983 | Volz et al. | |
| 4,479,271 A | 10/1984 | Bolesky et al. | |
| 4,538,306 A | 9/1985 | Dorre et al. | |
| 4,659,331 A | 4/1987 | Matthews et al. | |
| 4,725,280 A | 2/1988 | Laure | |
| 4,759,768 A | 7/1988 | Hermann et al. | |
| 4,822,364 A | 4/1989 | Inglis et al. | |
| 4,911,719 A | 3/1990 | Merle et al. | |
| 4,927,422 A | 5/1990 | Engelhardt | |
| 4,936,853 A | 6/1990 | Fabian et al. | |
| 5,024,670 A | 6/1991 | Smith et al. | |
| 5,030,237 A | 7/1991 | Sorbie et al. | |
| 5,207,711 A | 5/1993 | Caspari et al. | |
| 5,282,867 A | 2/1994 | Mikhail | |
| 5,314,484 A | 5/1994 | Huene | |
| 5,376,121 A | 12/1994 | Huene et al. | |
| 5,380,334 A | 1/1995 | Torrie et al. | |
| 5,411,555 A | 5/1995 | Nieder | |
| 5,507,821 A | 4/1996 | Sennwald et al. | |
| 5,507,826 A | 4/1996 | Besselink et al. | |
| 5,549,685 A | 8/1996 | Hayes | |
| 5,584,835 A | 12/1996 | Greenfield | |
| 5,665,087 A | 9/1997 | Huebner | |
| 5,702,471 A | 12/1997 | Grundei et al. | |
| 5,725,541 A | 3/1998 | Anspach, III et al. | |
| 5,725,591 A | 3/1998 | DeCarlo, Jr. et al. | |
| 5,782,923 A | 7/1998 | Engelbrecht et al. | |
| 5,840,078 A | 11/1998 | Yerys | |
| 5,879,395 A | 3/1999 | Tornier et al. | |
| 5,980,557 A | 11/1999 | Iserin et al. | |
| 6,027,534 A | 2/2000 | Wack et al. | |
| 6,120,543 A | 9/2000 | Kubein-Meesenburg et al. | |
| 6,162,253 A | 12/2000 | Conzemius et al. | |
| 6,290,725 B1 | 9/2001 | Weiss et al. | |
| 6,306,171 B1 | 10/2001 | Conzemius | |
| 6,379,387 B1 | 4/2002 | Tornier et al. | |
| 6,626,906 B1 | 9/2003 | Young | |
| 6,656,225 B2 | 12/2003 | Martin | |
| 6,699,290 B1 | 3/2004 | Wack et al. | |
| 6,767,368 B2 | 7/2004 | Tornier et al. | |
| 6,814,757 B2 | 11/2004 | Kopylov et al. | |
| 6,890,357 B2 | 5/2005 | Tornier | |
| 7,247,170 B2 | 7/2007 | Graham et al. | |
| 7,527,650 B2 | 5/2009 | Johnson et al. | |
| 2002/0165614 A1* | 11/2002 | Tornier | 623/20.12 |
| 2004/0186580 A1 | 9/2004 | Steinmann | |
| 2004/0243243 A1 | 12/2004 | Tornier | |
| 2004/0254574 A1 | 12/2004 | Morrison et al. | |
| 2005/0216090 A1 | 9/2005 | O'Driscoll et al. | |
| 2006/0173546 A1 | 8/2006 | Berelsman et al. | |
| 2006/0247786 A1 | 11/2006 | Ball | |
| 2008/0015706 A1 | 1/2008 | Berelsman et al. | |
| 2008/0033566 A1 | 2/2008 | Berelsman et al. | |
| 2008/0154384 A1 | 6/2008 | Acker et al. | |
| 2008/0183291 A1 | 7/2008 | Scheller et al. | |
| 2008/0188942 A1 | 8/2008 | Brown et al. | |
| 2009/0105839 A1 | 4/2009 | Ikegami et al. | |
| 2010/0087928 A1 | 4/2010 | Graham et al. | |
| 2010/0179661 A1 | 7/2010 | Berelsman et al. | |
| 2010/0222887 A1 | 9/2010 | Katrana et al. | |
| 2012/0136450 A1* | 5/2012 | Wendelburg et al. | 623/20.11 |

FOREIGN PATENT DOCUMENTS

| | | |
|---|---|---|
| EP | 1051954 A1 | 11/2000 |
| EP | 1481653 A1 | 12/2004 |
| FR | 2419718 A1 | 10/1979 |
| FR | 2634373 | 1/1990 |
| GB | 1520162 | 8/1978 |
| RU | SU1560183 A | 7/1988 |
| RU | SU1567200 A | 5/1990 |

OTHER PUBLICATIONS

Non-Final Office Action for U.S. Appl. No. 12/391,904, mailed Nov. 1, 2012.

Non-Final Office Action regarding U.S. Appl. No. 12/780,424, mailed Nov. 2, 2012.

Non-Final Office Action regarding U.S. Appl. No. 12/562,616, mailed May 17, 2012.

DePuy Orthopaedics, Inc., web page print out—http://www/allaboutarthritis.com/AllAbout Arthritis/layoutTemplates/html/en/contentdisplay/document/condition/arthritis/clinicalArticle/Elbow_Replacement_Surgery.htm, 2000-2005—printed Dec. 14, 2005.

Discovery Elbow System brochure, Surgical Technique, Biomet Orthopedics, Inc., ã2002.

Joint Replacement, Overview, ãDePuy Orthopaedics, Inc., www.jointreplacement.com/xq/ASP.default/mn.local/pg.list/joint_id.2/list_id.59/newFont.2/joint_nm.Elbow/local_id.18/qx/default.htm, 2000-2005.

Joint Replacement, Surgery, ãDePuy Orthopaedics, Inc., www.jointreplacement.com/xq/ASP.default/mn.local/pg.list/joint_id.2/list_id.59/newFont.2/joint_nm.Elbow/local_id.18/qx/default.htm, 2000-2005.

International Search Report for PCT/US01/22338 mailed Jan. 3, 2002 based on Provisional U.S. Appl. No. 60/219,103, filed Jul. 18, 2000.

Latitudeâ"Total Elbow Prosthesis, A new generation is born naturally precise", TORNIER [undated].

Latitudeâ"Total Elbow Prosthesis, Surgical Technique", TORNIER pp. 1-39 [undated].

Sorbie-QuestorâTotal Elbow System, Extremities (2003) Wright Medical Technology, Inc., 1 page.

Non-Final Office Action for U.S. Appl. No. 11/384,943, mailed Apr. 13, 2010.

Final Office Action for U.S. Appl. No. 11/384,943, mailed Oct. 27, 2010.

Non-Final Office Action for U.S. Appl. No. 11/384,943, mailed Apr. 12, 2011.

International Search Report and Written Opinion for PCT/US2009/057449 mailed Feb. 21, 2011.

International Search Report and Written Opinion for PCT/US2010/049314 mailed Feb. 21, 2011.

International Preliminary Report on Patentability and Written Opinion for PCT/US2009/057449 Mailed Sep. 9, 2011.

* cited by examiner

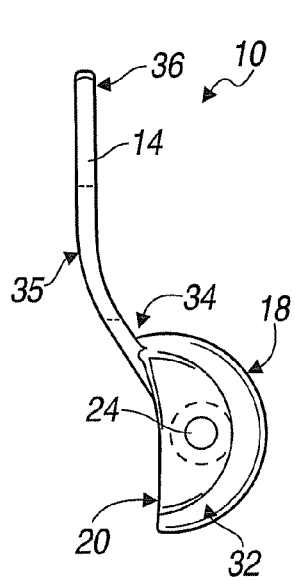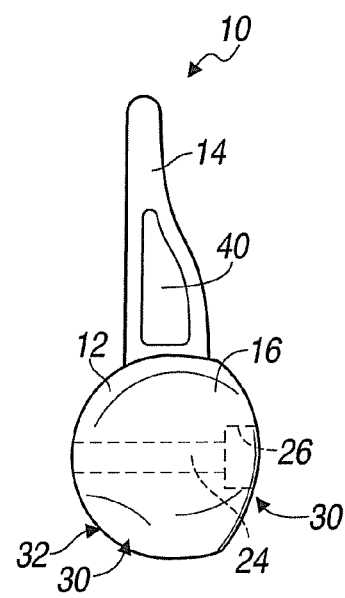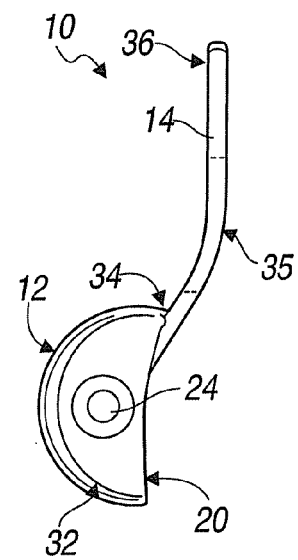
FIG. 1A  FIG. 1B  FIG. 1C
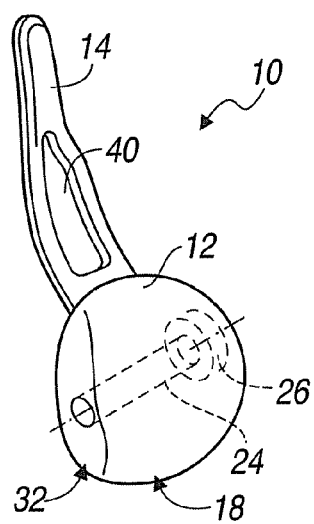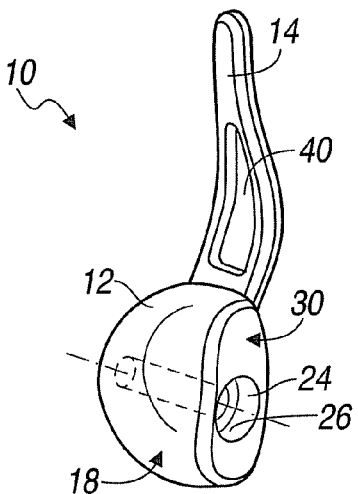
FIG. 1D  FIG. 1E

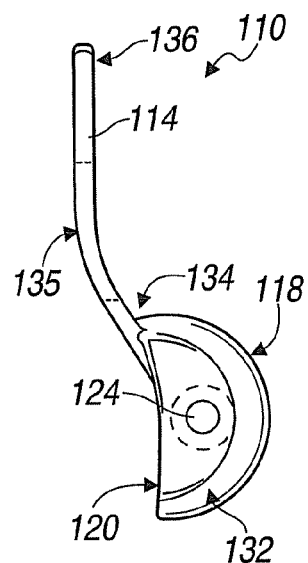 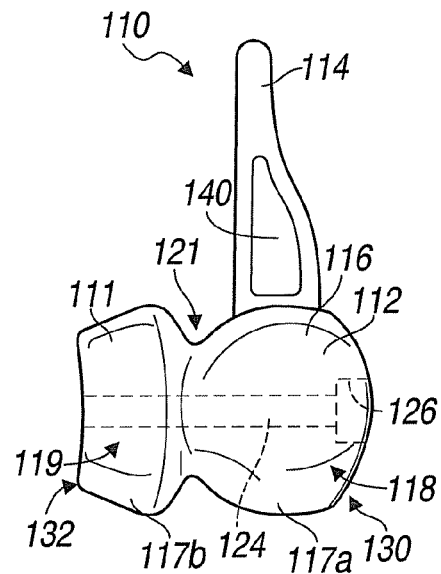 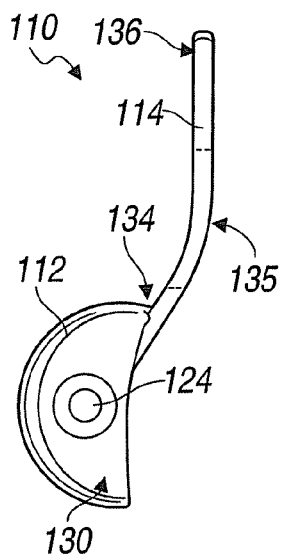
FIG. 3A  FIG. 3B  FIG. 3C
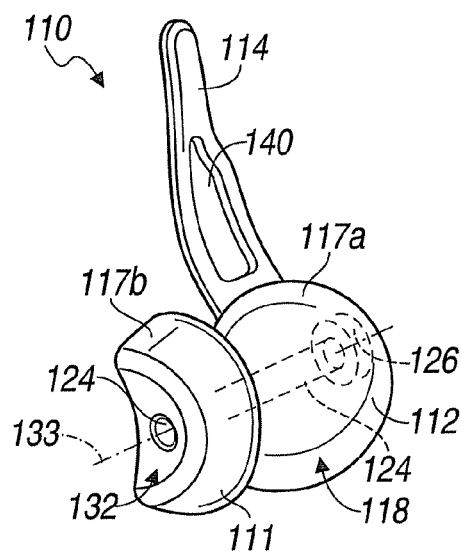 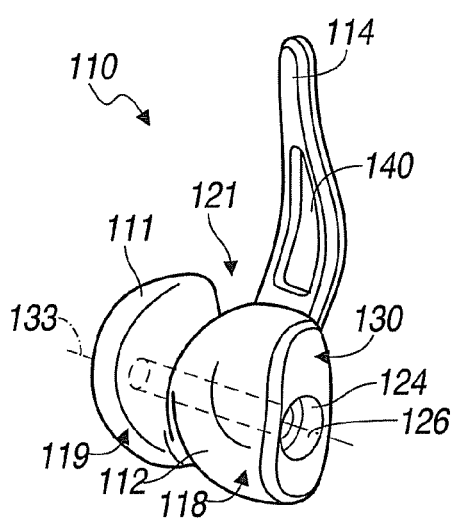
FIG. 3D  FIG. 3E

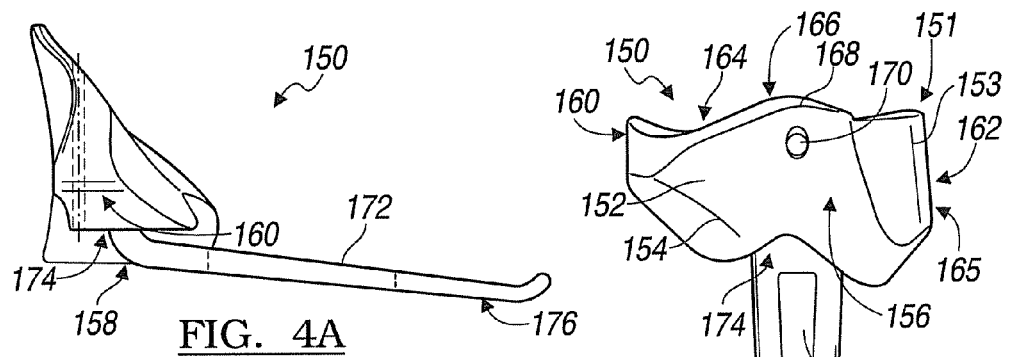
FIG. 4A  FIG. 4B
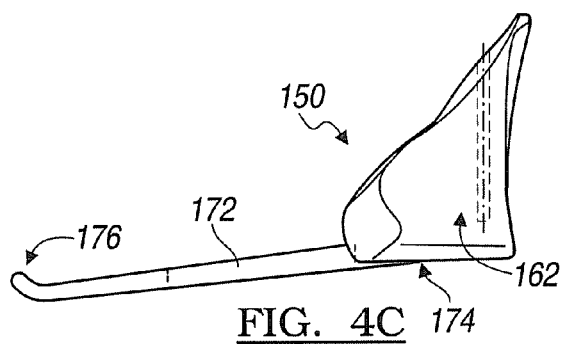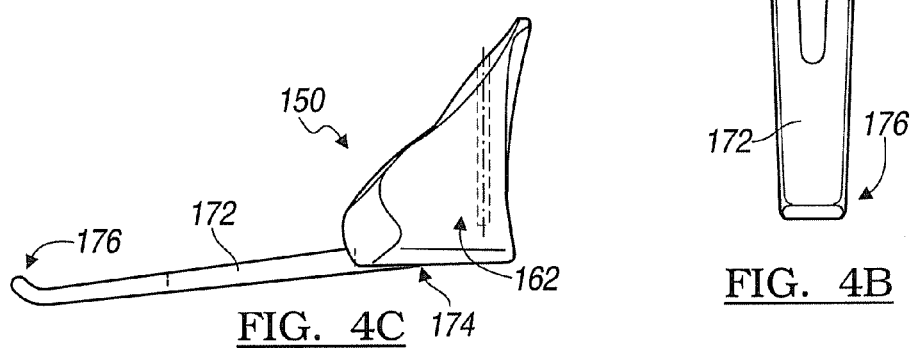
FIG. 4C
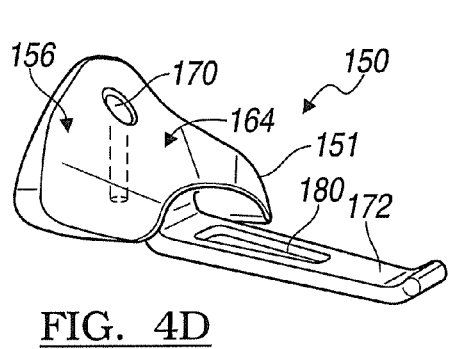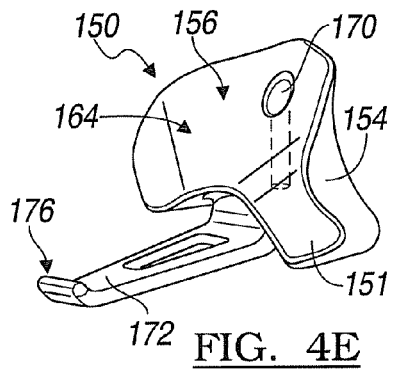
FIG. 4D  FIG. 4E
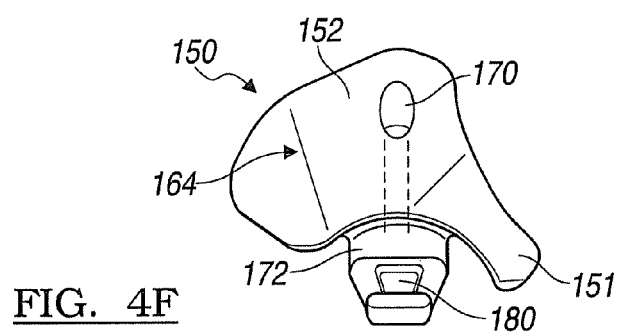
FIG. 4F

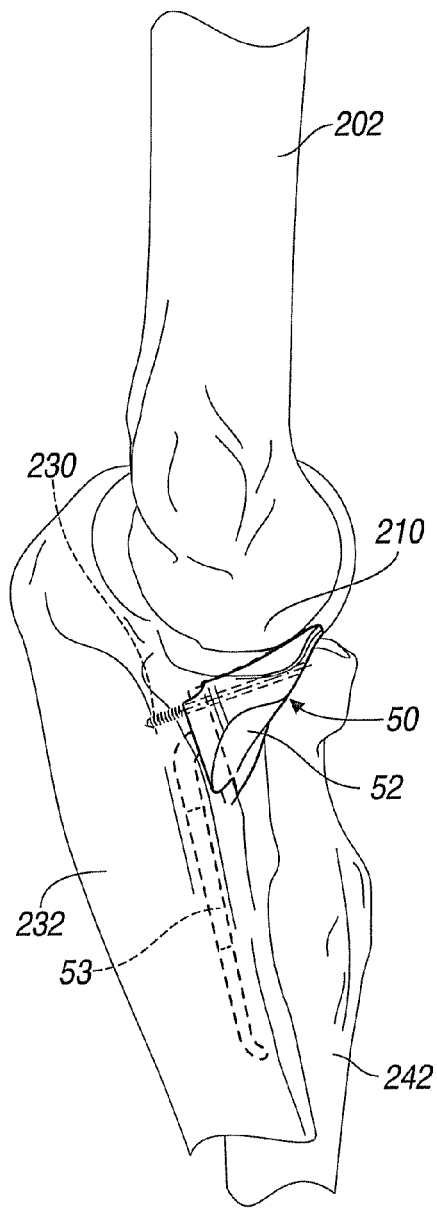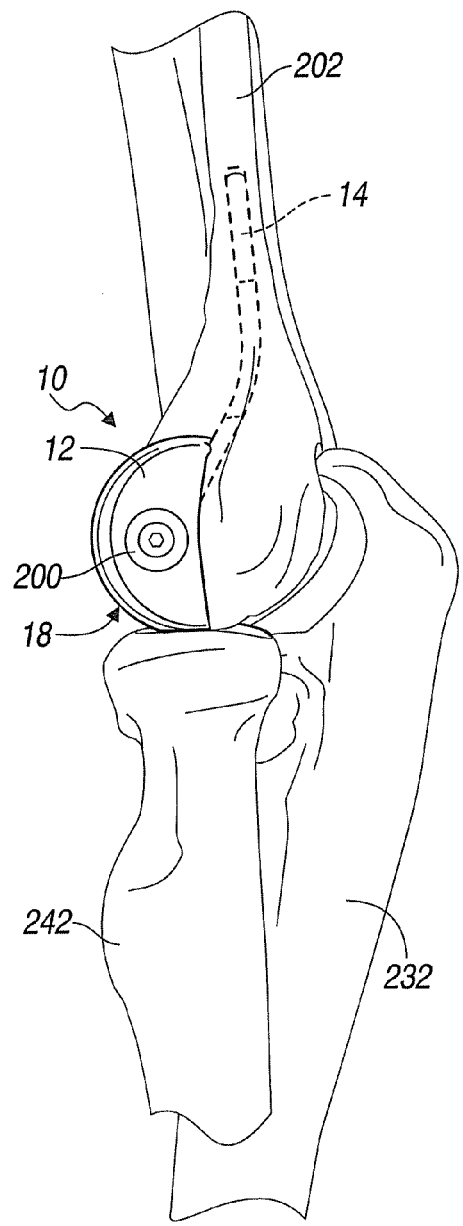
FIG. 5E                    FIG. 5F

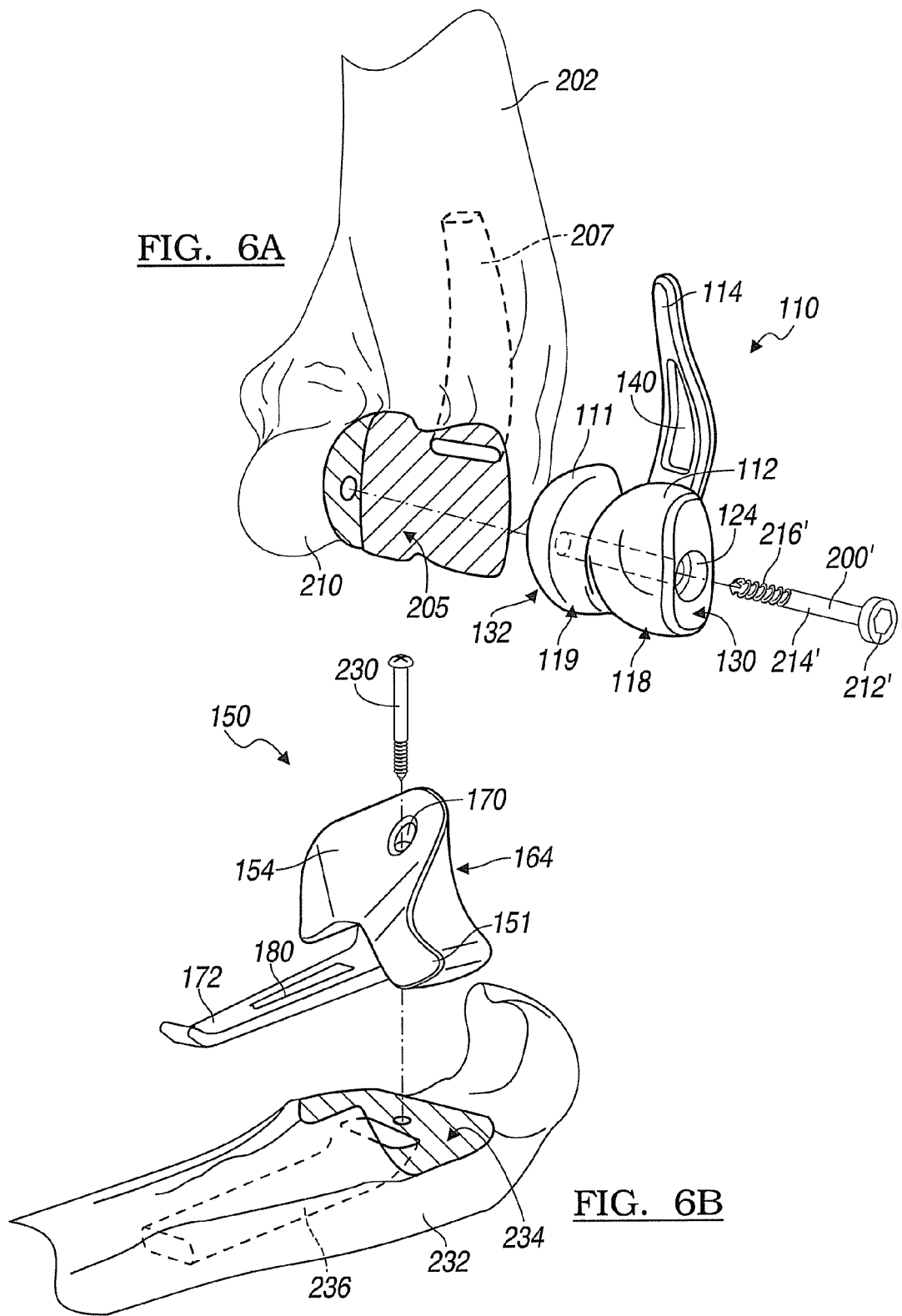

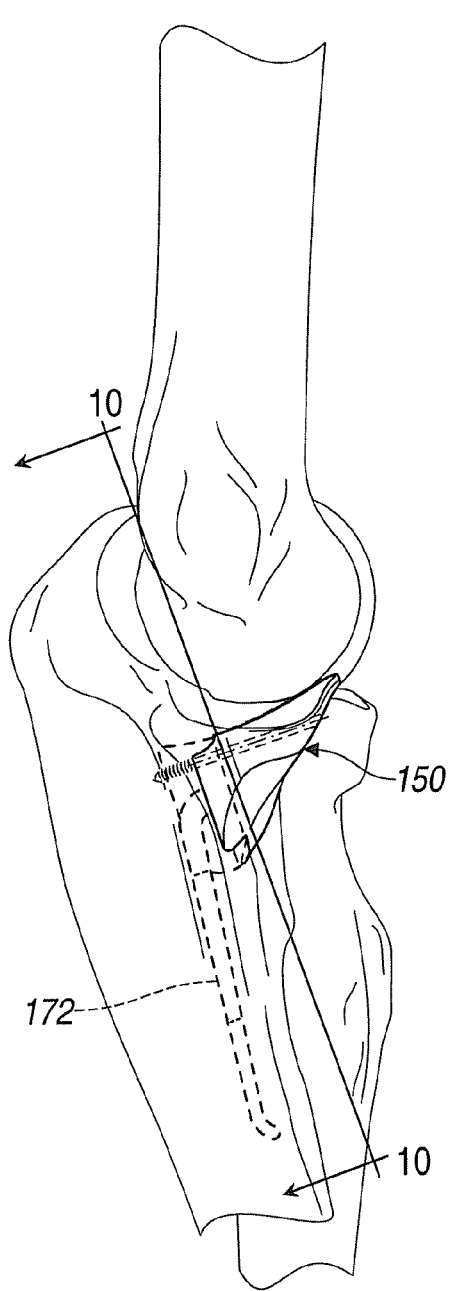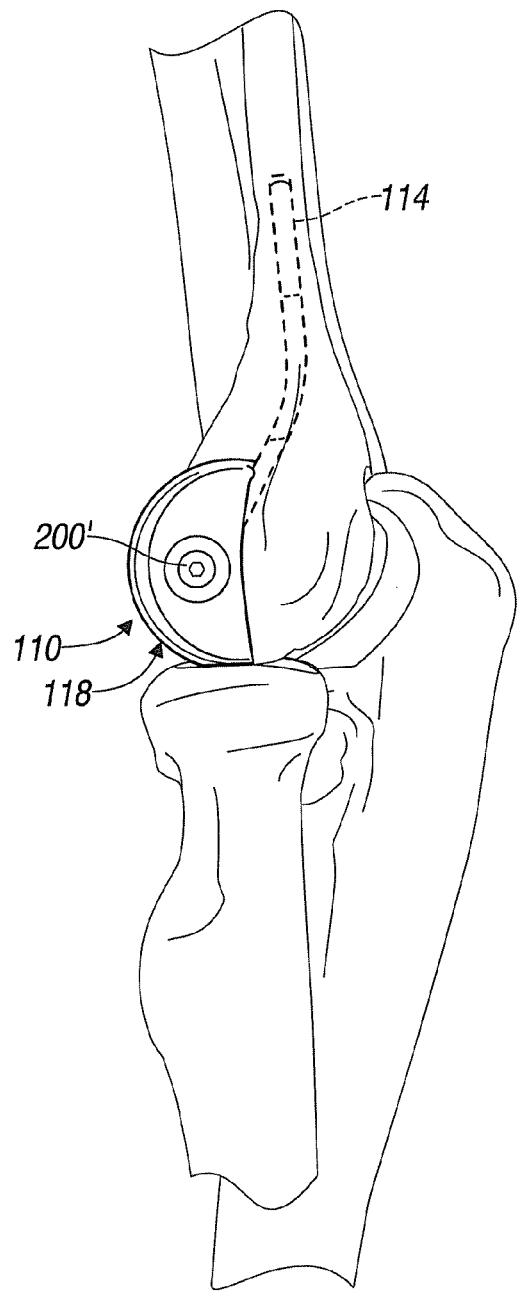
FIG. 6E
FIG. 6F

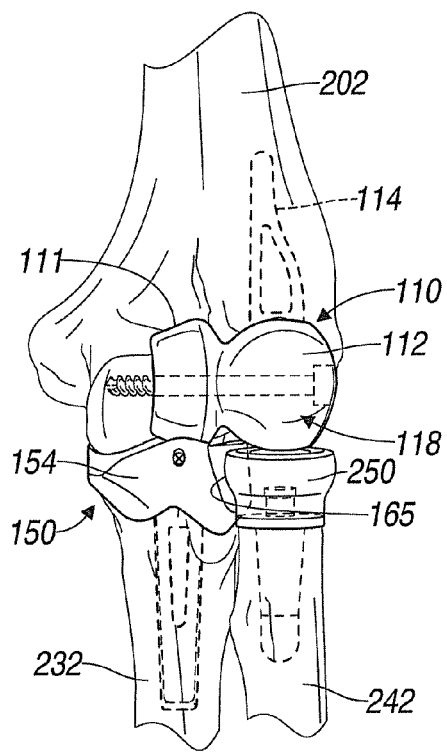
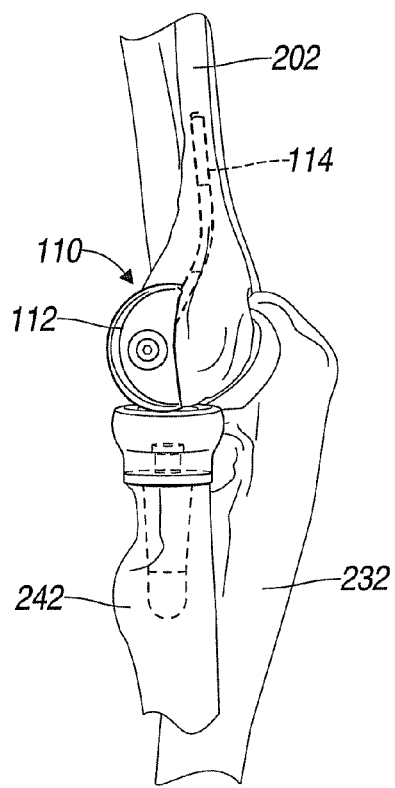
FIG. 11A     FIG. 11B
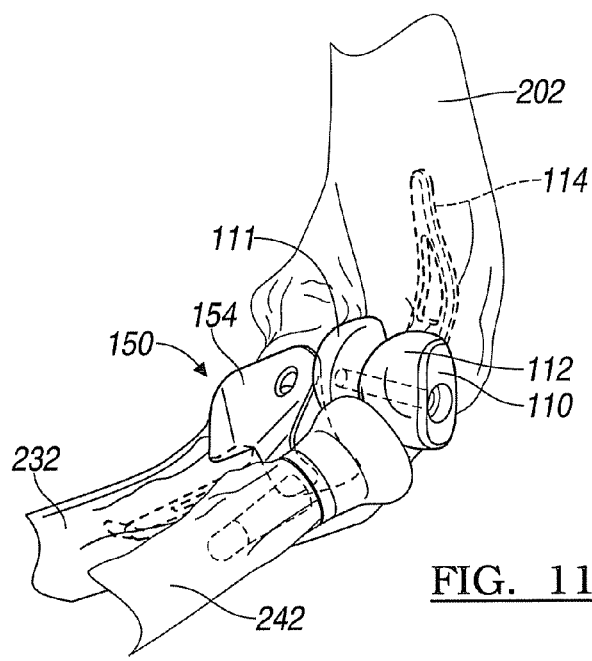
FIG. 11C

ELBOW PROSTHESIS

CROSS-REFERENCE TO RELATED APPLICATIONS

This application is a continuation-in-part of U.S. patent application Ser. No. 12/562,616 filed on Sep. 18, 2009. The entire disclosures of the above applications are incorporated herein by reference.

FIELD

The present teachings relate generally to prosthetic devices used in arthroplasty and more particularly to a modular elbow prosthesis.

BACKGROUND

The present teachings relate generally to prosthetic devices used in arthroplasty and more particularly to a modular elbow prosthesis including a capitellar implant and a coronoid implant.

In general, elbow prostheses have been provided and can generally include linked and unlinked versions. Linked or constrained elbow prostheses are known which comprise simple hinge arrangements, one component of which is attached to the end of the humerus and the other component of which is attached to the end of the ulna. The humeral component includes a shaft, that is cemented (or press-fit uncemented) into a prepared cavity in the end of the humerus, and the ulnar component includes a shaft, that is cemented (or press-fit uncemented) to the end of the ulna. The components of the prosthesis are connected together by means of a hinge pin so that the prosthesis allows a single degree of freedom of movement of the ulna relative to the humerus. Unlinked, or unconstrained, elbow prostheses are known which are similar to linked elbow prostheses but do not have a specific component which mechanically couples the humeral and ulnar stems together. Rather, the prosthetic device is held together by the patient's natural soft tissues.

In some instances, it may be desirable to replace portions of bone in an elbow, such as to address certain fractures. Some fractures, such as about the capitellum and coronoid can be the most technically challenging to reconstruct. Difficult exposure, inconsistent fracture fragment size, poor bone quality and other factors conspire to result in suboptimal outcomes such as nonunion, instability and accelerated arthritis. Furthermore, in some examples it may be desirable to connect a capitellar implant posteriorly of its articulating surface to take advantage of substantial host trochlear bone.

SUMMARY

This section provides a general summary of the disclosure, and is not a comprehensive disclosure of its full scope or all of its features.

An elbow prosthesis can include a capitellar implant that has an articulating head and a stem. The articulating head can have a first substantially hemispherical portion and a second portion that collectively extend between lateral and medial sides of the articulating head and are separated by a plane. The first and second portions can generally extend between the lateral and medial sides. The second portion can generally have an attachment lobe that extends on the lateral side and that defines a passage therethrough. The passage can extend at least partially on the second portion.

According to additional features, the passage can extend through the attachment lobe at a location entirely on the second portion. The attachment lobe can further define a counterbore formed concentrically with the passage. A bone screw having a shank and a head can be provided. The shank can have a length that is greater the passage through the articulating head, such that the head nests in the counterbore and at least a portion of the shank extends proud from the attachment lobe in an implanted position.

According to other features, the stem can be generally planar in a medial/lateral direction and include a connecting end and a proximal end. The connecting end can be attached to the articulating head. The stem can have a curved intermediate portion that positions the proximal end posteriorly relative to the connecting end in an implanted position. According to other features, the articulating head can be modular and be adapted to be selectively coupled to the stem. In other arrangements, the stem can be intraoperatively coupled to the articulating head. The stem can include a first interlocking geometry formed at the connecting end. The articulating head can include a second interlocking geometry. The first and second interlocking geometries can mate in an assembled position. Next, the first interlocking geometry can include one of a T-shaped male insertion portion and a T-shaped female receiving portion. The second interlocking geometry can include the other of the male and female receiving portions. The T-shaped female receiving portion can slidably receive the T-shaped male insertion portion. A throughbore can be defined through the first and second interlocking geometries that accommodates a securing member in an implanted position. The throughbore can be defined exclusively on the first substantially hemispherical portion. According to other features, a plurality of stems having differing geometries can be provided that each have a connecting end that is selectively and alternatively attached to the articulating head.

Further areas of applicability will become apparent from the description provided herein. The description and specific examples in this summary are intended for purposes of illustration only and are not intended to limit the scope of the present disclosure.

DRAWINGS

Additional advantages and features of the present teachings will become apparent from the subsequent description and the appended claims, taken in conjunction with the accompanying drawings, wherein:

FIG. 1A is a medial view of a capitellar implant constructed in accordance to the present teachings;

FIG. 1B is an anterior view of the capitellar implant of FIG. 1A;

FIG. 1C is a lateral view of the capitellar implant of FIG. 1A;

FIG. 1D is a perspective medial view of the capitellar implant of FIG. 1A;

FIG. 1E is a perspective lateral view of the capitellar implant of FIG. 1A;

FIG. 3A is a medial view of a capitellar implant constructed in accordance to other features of the present teachings;

FIG. 3B is an anterior view of the capitellar implant of FIG. 3A;

FIG. 3C is a lateral view of the capitellar implant of FIG. 3A;

FIG. 3D is a perspective medial view of the capitellar implant of FIG. 3A;

FIG. 3E is a perspective lateral view of the capitellar implant of FIG. 3A;

FIG. 4A is a medial view of a coronoid implant constructed in accordance to another example of the present teachings;

FIG. 4B is an anterior view of the coronoid implant of FIG. 4A;

FIG. 4C is a lateral view of the coronoid implant of FIG. 4A;

FIG. 4D is a perspective medial view of the coronoid implant of FIG. 4A;

FIG. 4E is a perspective lateral view of the coronoid implant of FIG. 4A;

FIG. 4F is an inferior view of the coronoid implant of FIG. 4A;

FIG. 5E is a medial view of a left elbow in extension shown with the coronoid implant of FIGS. 2A-2F implanted relative to a host ulna;

FIG. 5F is a lateral view of a left elbow in extension shown with the capitellar implant of FIGS. 1A-1E implanted relative to a distal humerus;

FIG. 6A is a lateral perspective view of the capitellar implant of FIGS. 3A-3E and a bone screw shown adjacent to a prepared distal humerus where a portion of the trochlea has been resected to accommodate an extension portion of the capitellar implant;

FIG. 6B is a lateral perspective view of the coronoid implant of FIGS. 4A-4F shown with a bone screw and adjacent to a prepared ulna;

FIG. 6E is a medial view of the coronoid implant of FIGS. 4A-4F shown implanted into a host ulna of a left elbow in extension;

FIG. 6F is a lateral view of the capitellar implant of FIGS. 3A-3E shown implanted into a host humerus and with the elbow in extension;

FIG. 11A is an anterior view of the capitellar and coronoid implants of FIGS. 3A-4F shown cooperating with a radial implant of a left elbow in extension;

FIG. 11B is a lateral view of the capitellar and radial implants of FIG. 11A and shown with the elbow in extension;

FIG. 11C is a lateral perspective view of a left elbow and shown with the capitellar, coronoid and radial implants of FIG. 11A;

Corresponding reference numerals indicate corresponding parts throughout the several views of the drawings.

DETAILED DESCRIPTION

Figure 2A:
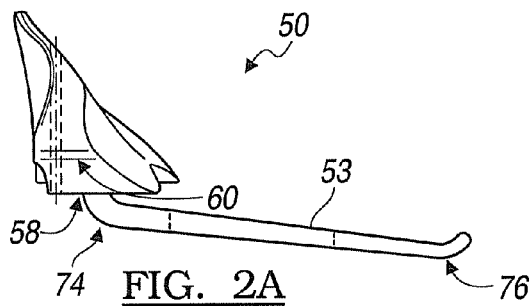
FIG. 2A is a medial view of a coronoid implant constructed in accordance to one example of the present teachings.
Figure 2B:
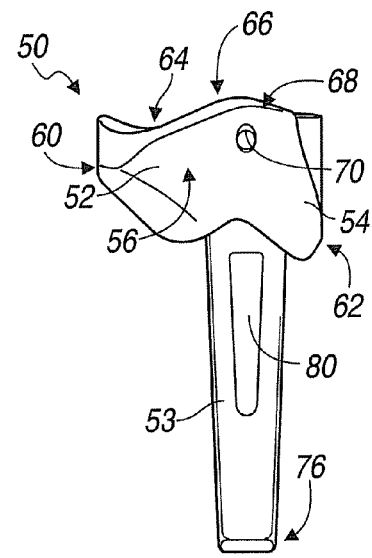
FIG. 2B is an anterior view of the coronoid implant of FIG. 2A.

The following description is merely exemplary in nature and is not intended to limit the present disclosure, application, or uses. It should be understood that throughout the drawings, corresponding reference numerals indicate like or corresponding parts and features.

At the outset, the following discussion and related figures relate to elbow prostheses including capitellar and coronoid implants constructed for implantation into a left elbow, however, it will be appreciated that the same implants can similarly be provided for a right elbow. In this way, a right capitellar and/or coronoid implant can be formed similarly but geometrically inversed in the medial/lateral direction.

With initial reference to FIGS. 1A-1E, a capitellar implant 10 constructed in accordance to one example of the present teachings will be described. In general, the capitellar implant 10 can be implanted at the distal humerus (FIG. 5A) in circumstances where it is desirable to accommodate fracture patterns along the articulating surfaces or other informalities observed about the distal humeral articular surface. The capitellar implant 10 generally comprises an articulating head 12 and a stem 14. The articulating head 12 can include an articulating body 16 having an arcuate articulating surface 18 and a humeral engaging surface 20. A passage 24 having a counterbore 26 can be formed through the articulating body 16 from a lateral side 30 to a medial side 32 of the articulating body 16. As will be described, the passage 24 is operable to receive a bone screw during implantation. As best illustrated in FIGS. 1A and 1C, the articulating surface 18 is generally hemispherical around the articulating body 16. The humeral engaging surface 20 can be generally concave such that the articulating surface 18 is provided around an area greater than 180 degrees of the articulating body 16. In some examples, the concave humeral engaging surface 20 can facilitate nesting of a prepared distal humerus. The humeral engaging surface 20 can be porous coated or roughened to further encourage bony ingrowth. As best illustrated in FIG. 1B, the anterior profile of the articulating body 16 can be generally circular and has a truncated lateral side 30. The lateral side 30 can generally provide a shallower radius relative to a remainder of the articulating body 16.

The articulating body 16 can be provided on a capitellar implant 10 having a geometry that substantially replicates at least portions of a natural capitellum of the patient. In this way, a plurality of capitellar implants 10 can be provided having articulating heads 12 with various geometries such that a surgeon can select an appropriate match based upon any given patient's particular needs or fracture areas.

The stem 14 can generally extend from a connecting end 34 that is attached to the articulating body 16 through a curved intermediate portion 35 to a proximal end 36. In general, the stem 14 can have a generally planar body that shifts posteriorly from the connecting end 34 through the curved intermediate portion 35 to the proximal end 36. The planar body can promote rotational stability. The stem 14 can define an opening 40 that can facilitate bone ingrowth when implanted into a prepared lateral column of a humerus. The opening 40 can have a generally triangular profile. In other examples, the opening 40 can be used to receive one or more bone screws for securably positioning the stem 14 relative to a humerus. While the figures described herein are directed toward implanting the stem 14 into a prepared lateral column of a humerus, the capitellar implant 10 can additionally or alternatively be positioned on an anterior face of a humerus. In one example, the stem 14 and/or the articulating head 12 can be formed of bio-compatible materials such as, but not limited to, any combinations of titanium, cobalt, polyethylene, pyrocarbon, PEEK, including carbon fiber reinforced PEEK, or other materials.

Figure 2C:
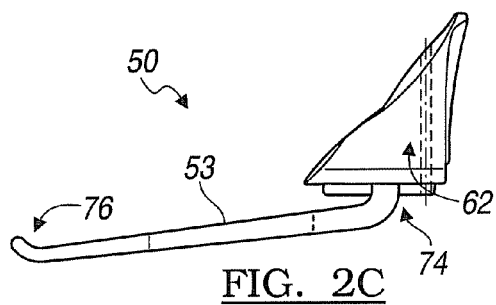
FIG. 2C is a lateral view of the coronoid implant of FIG. 2A.
Figure 2D:
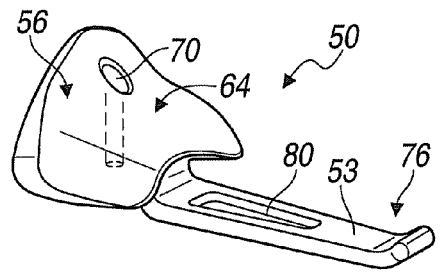
FIG. 2D is a perspective medial view of the coronoid implant of FIG. 2A.
Figure 2E:
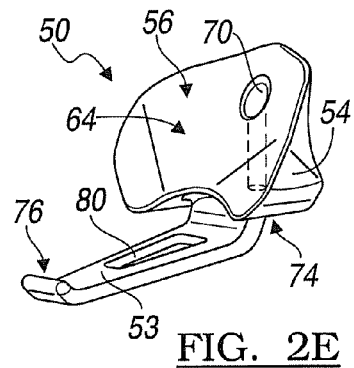
FIG. 2E is a perspective lateral view of the coronoid implant of FIG. 2A.
Figure 2F:
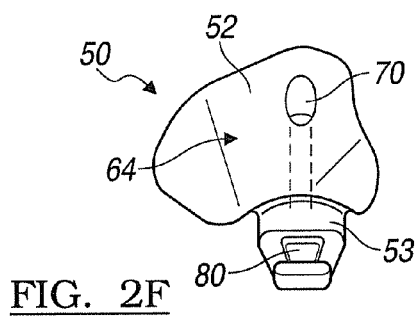
FIG. 2F is an inferior view of the coronoid implant of FIG. 2A.

With reference now to FIGS. 2A-2F, a coronoid implant 50 constructed in accordance with one example of the present teachings will be described. Again, the coronoid implant 50 is constructed for use with a left elbow. However, a similar coronoid implant can be provided for a right elbow having a similar geometry that is inversed in the medial/lateral direction. In general, the coronoid implant 50 can be implanted relative to a host ulna (FIG. 5B) to replace at least portions of a host coronoid that may have experienced a fracture or other defect. The coronoid implant 50 can generally comprise an articulating portion 52 and a stem 53. The articulating portion 52 can have a body 54 having a generally triangular wedge-like shape that extends between an anterior side 56 (FIG. 2A), a posterior side 58 (FIG. 2B), a medial side 60 (FIG. 2A), and a lateral side 62 (FIG. 2C). The body 54 can include a superior articulating surface 64, a central ridge 66 and an anterior buttress 68. In one example, the posterior side 58 has a non-planar profile that is operable to engage a prepared bone surface of an ulna. The non-planar profile can facilitate rotational stability. The central ridge 66 extends in the anterior/posterior direction. The anterior buttress 68 extends generally in the medial/lateral direction and is substantially transverse to the central ridge 66. A passage 70 is formed through the body 54 from the anterior side 56 to the posterior side 58. As will be described, the passage 70 is operable to receive a bone screw during implantation of the coronoid implant 50. The stem 53 can having a planar body that extends generally from a connecting end 74 to a distal end 76. The planar body of the stem 53 can promote rotational stability. In one example, the distal end 76 can be curved at a terminal tip in a generally anterior direction relative to a long axis of the stem 53. The stem 53 can define an opening 80. The opening 80 can facilitate boney ingrowth when implanted relative to an ulna. In other examples, the opening 80 can be adapted to receive one or more bone screws to further supplement fixation of the coronoid implant 50 relative to a host ulna.

Turning now to FIGS. 3A-3E, a capitellar implant 110 constructed in accordance with another example of the present teachings will be described. In general, the capitellar implant 110 can be formed similar to capitellar implant 10 as described above with respect to FIGS. 1A-1E, but additionally includes an extension portion 111. The capitellar implant 110 can be used in circumstances where it may be desirable to replace the lateral trochlear, or portions thereof, in instances where a more extensive coronal shear pattern or other defect may be observed in the host capitellum.

The capitellar implant 110 generally comprises an articulating head 112 and a stem 114. The articulating head 112 can include an articulating body 116 having a pair of bulbous portions 117a and 117b that have a first arcuate articulating surface 118 and a second arcuate articulating surface 119, respectively. The articulating body 116 can also include a humeral engaging surface 120. The bulbous portions 117a and 117b can be laterally offset by a narrowed region 121. The second arcuate articulating surface 119 can be provided on the extension portion 111. A passage 124 having a counterbore 126 can be formed through the articulating body 116 from a lateral side 130 to a medial side 132 of the articulating body 116. As will be described, the passage 124 is operable to receive a bone screw during implantation of the capitellar implant 110. The respective first and second articulating surfaces 118 and 119 can be centered about a common axis 133. The axis 133 can be coaxial with the passage 124. The articulating body 116 can be provided on a capitellar implant 110 having a geometry that substantially replicates at least portions of a natural capitellum and trochlea of a patient. In this way, a plurality of capitellar implants 110 can be provided having articulating heads 112 with various geometries such that a surgeon can select an appropriate match based upon any given patient's particular needs. The stem 114 can generally extend from a connecting end 134 that is attached to the articulating body 116 through a curved intermediate portion 135 to a proximal end 136. In general, the stem 114 shifts posteriorly from the connecting end 134 through the curved intermediate portion 135 to the proximal end 136. The stem 114 can define an opening 140 that can facilitate bone ingrowth when implanted into a prepared lateral column of a humerus. In other examples, the opening 140 can be used to receive one or more bone screws for securably positioning the stem 114 relative to a humerus. The capitellar implant 110 can additionally or alternatively be positioned such that the stem 114 is positioned on an anterior face of the humerus. In one example, the stem 114 and/or the articulating head 112 can be formed of bio-compatible materials such as, but not limited to, any combinations or titanium, cobalt, polyethylene, pyrocarbon, PEEK, including carbon fiber reinforced PEEK, or other materials.

With reference now to FIGS. 4A-4F, a coronoid implant 150 constructed in accordance with one example of the present teachings will be described. In general, the coronoid implant 150 can be implanted relative to a host ulna to replace at least portions of a host coronoid that may have experienced a fracture or other defect. The coronoid implant 150 is constructed similar to the coronoid implant 50 as described above with respect to FIGS. 2A-2F and further includes a lateral extension portion 151. The lateral extension portion 151 can be particularly useful in instances where it is desirable to accommodate varying amounts of the lesser sigmoid fossa, which articulates with the radial head.

The coronoid implant 150 can generally comprise a first articulating portion 152 and a second articulating portion 153. The first and second articulating portions 152 and 153 can be formed on a generally triangular wedge-shaped body 154 that extends between an anterior side 156 (FIG. 4B), a posterior side 158 (FIG. 4A), a medial side 160 (FIG. 4A), and a lateral side 162 (FIG. 4C). The body 154 can include a superior articulating surface 164 provided on the first articulating portion 152 and a radial articulating surface 165 provided on the second articulating portion 153. The body 154 can further include a central ridge 166 and an anterior buttress 168. In one example, the posterior side 158 has a non-planar profile that is operable to engage a prepared bone surface of an ulna. The non-planar profile can facilitate rotational stability. The central ridge 166 extends in the anterior/posterior direction. The anterior buttress 168 extends generally in the medial/lateral direction and is substantially transverse to the central ridge 166. A passage 170 is formed through the body 154 from the anterior side 156 to the posterior side 158. As will be described, the passage 170 is operable to receive a bone screw during implantation of the coronoid implant 150. A stem 172 can have a planar body that extends generally from a connecting end 174 to a distal end 176. In one example, the distal end 176 can be curved at a terminal tip in a generally anterior direction relative to a long axis of the stem 172. The stem 172 can define an opening 180. The opening 180 can facilitate boney ingrowth when implanted relative to an ulna. In other examples, the opening 180 can be adapted to receive one or more bone screws to further supplement fixation of the coronoid implant 150 relative to a host ulna.

Figure 5A:
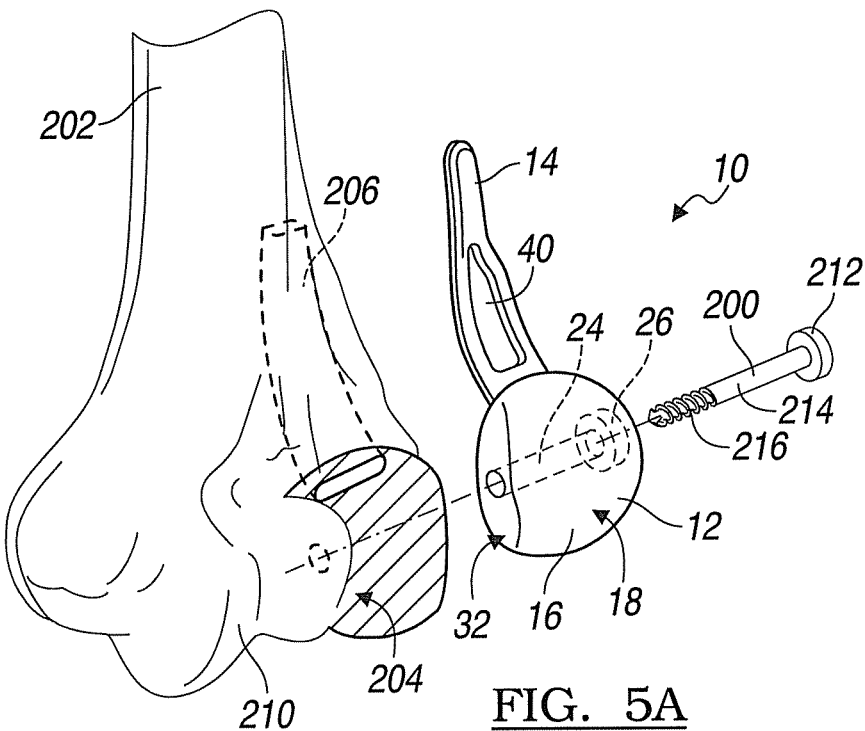
FIG. 5A is an exploded medial perspective view of the capitellar implant of FIGS. 1A-1E and a bone screw shown prior to implantation onto a prepared distal left humerus.

With reference now to FIG. 5A, the capitellar implant 10 is shown with a bone screw 200 adjacent to a humerus 202. An implant engaging surface 204 can be prepared on the distal humerus subsequent to resecting at least portions of a capitellum. In some examples, the implant engaging surface 204 can be milled or cut in a non-planar shape that corresponds to the humeral engaging surface 20. A passage 206 can be prepared that can correspond with alignment to an lateral column of the humerus 202. It is appreciated that the surface 204 and the passage 206 may take other forms than that shown in the example of FIG. 5A. However, it will be appreciated that the capitellar implant 10 can be implanted onto a distal humerus to accommodate coronal shear fractures involving the lateral aspect of a trochlea 210. The bone screw 200 can include a head 212 and a shank 214 having a threaded end 216. As will become appreciated, the axial length of the bone screw 200 is greater than the width of the body 16 from the lateral side 30 to the medial side 32 of the articulating head 12, such that at least portions of the threaded end 216 can extend proud from the medial side 32 of the articulating head 12. In one example, the head 212 can provide a geometry substantially complementary to the counterbore 26 provided in the body 16.

Figure 5B:
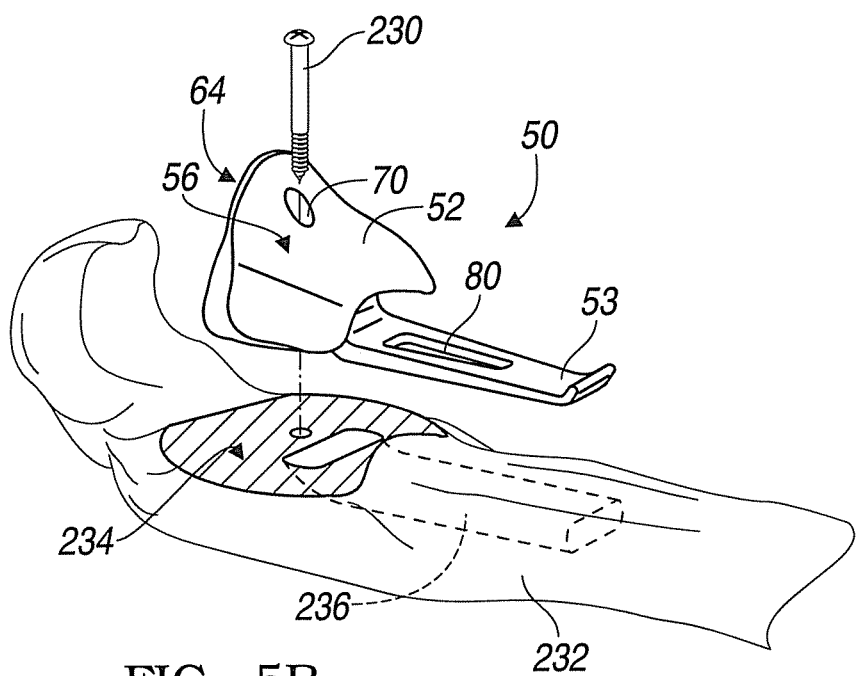
FIG. 5B is an exploded medial perspective view of the coronoid implant of FIGS. 2A-2F and a bone screw shown adjacent to a prepared proximal left ulna.

Turning now to FIG. 5B, the coronoid implant 50 is shown in exploded view with a bone screw 230 and adjacent to an ulna 232. In the example shown in FIG. 5B, the ulna 232 includes an implant engaging surface 234 where a host coronoid has been resected from the ulna 232. In some examples, the implant engaging surface 234 can be milled or cut in a non-planar shape that corresponds to the posterior side 58. A passage 236 can be prepared in the ulna 232. In one example, the passage 236 can correspond with an intramedullary canal of the host ulna. It will be appreciated that the particular geometry of the surface 234 and the passage 236 is merely exemplary and the host ulna 232 may be prepared differently according to the needs of a particular patient.

Figure 5C:
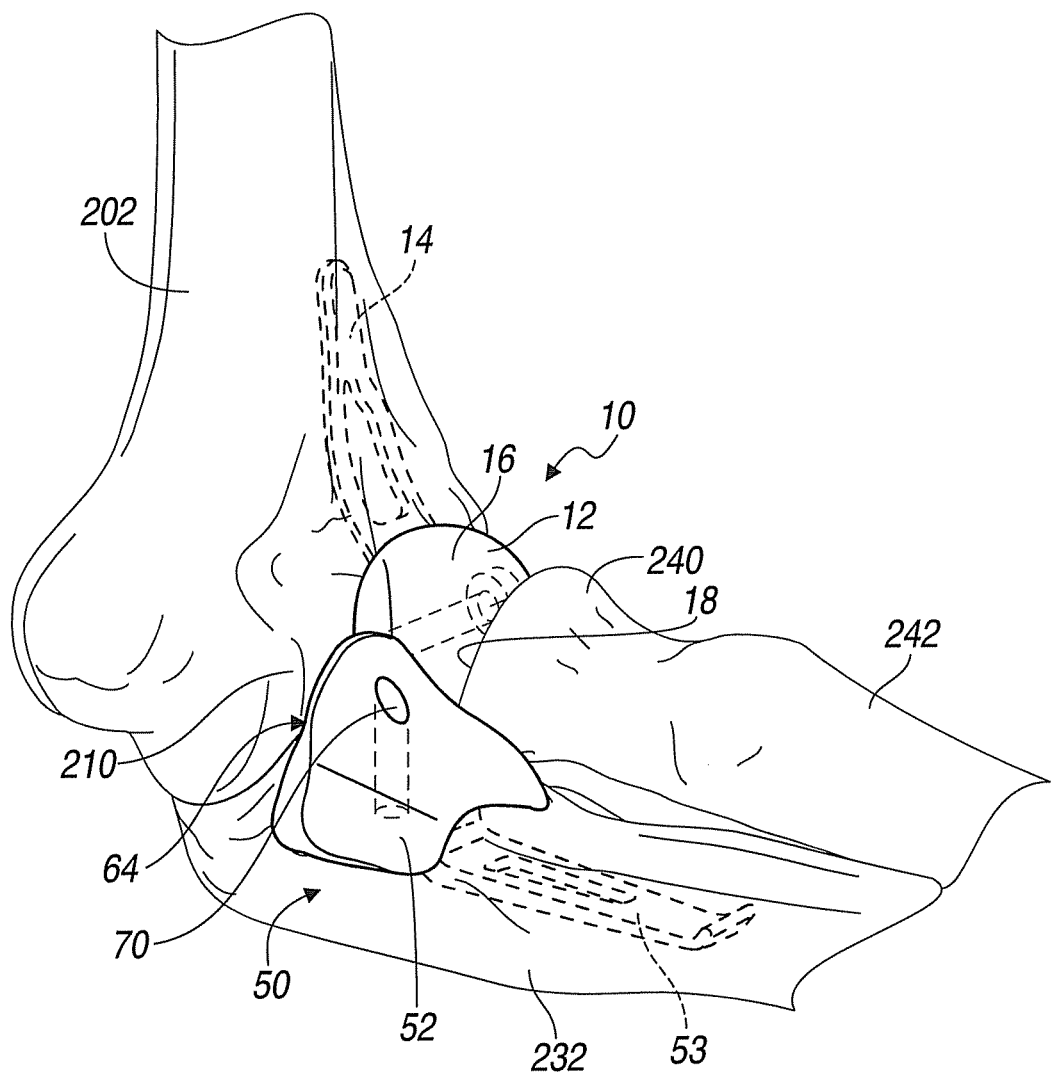
FIG. 5C is an exemplary implanted position of the capitellar and coronoid implants of FIGS. 1A-2F according to one example.
Figure 5D:
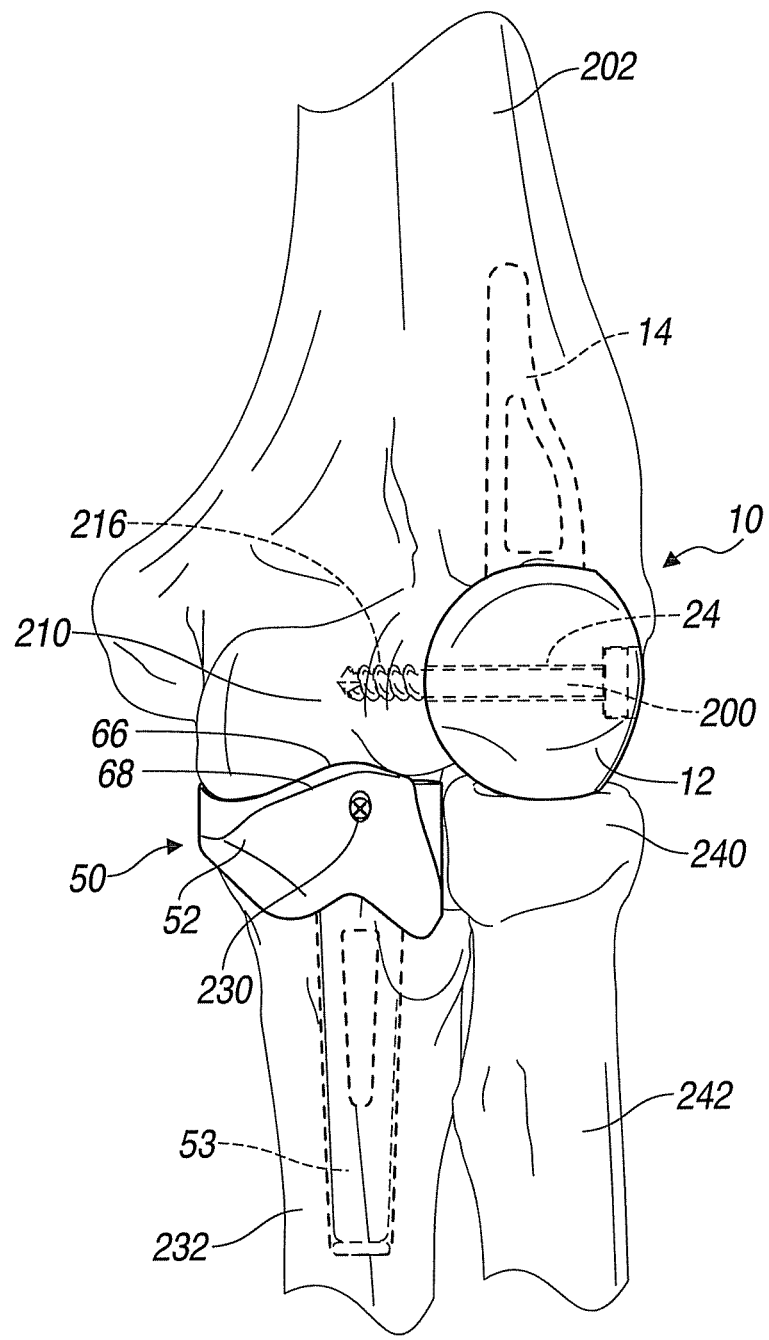
FIG. 5D is an anterior view of the implanted capitellar and coronoid implants shown in FIG. 5C.

Turning now to FIG. 5C, the capitellar implant 10 and the coronoid implant 50 are shown implanted into an exemplary left elbow. For clarity, the bone screws 200 and 230 have been omitted from the illustration in FIG. 5C. As shown, the articulating surface 18 of the articulating body 16 of the capitellar implant 10 can be aligned for articulation with a head 240 of a radius 242. The coronoid implant 50 can be positioned relative to the ulna 232, such that the superior articulating surface 64 is aligned for slidable articulation with the trochlea 210. As shown in FIG. 5D, the capitellar implant 10 and the coronoid implant 50 are illustrated in an implanted position relative to a left elbow in extension. Notably, the bone screw 200 has been passed through the passage 24 from a lateral to a medial direction, such that the threaded end 216 threadably advances into the trochlea 210. The bone screw 200 therefore can provide additional fixation of the capitellar implant 10 relative to the host humerus 202 in addition to the fixation properties provided by the stem 14. It will be appreciated that bone screws having a longer shaft (than depicted in the Figs.) may be used when it may be desired to penetrate further into the trochlear. In addition, the bone screw 230 is shown advanced through the passage 70 provided in the articulating portion 52 of the coronoid implant 50. The bone screw 230 can threadably advance into the host ulna 232 to provide supplemental fixation of the coronoid implant 50 relative to the ulna 232 in addition to the stem 53. In some examples, bone cement may also be used such as around the stem 14.

Figure 5G:
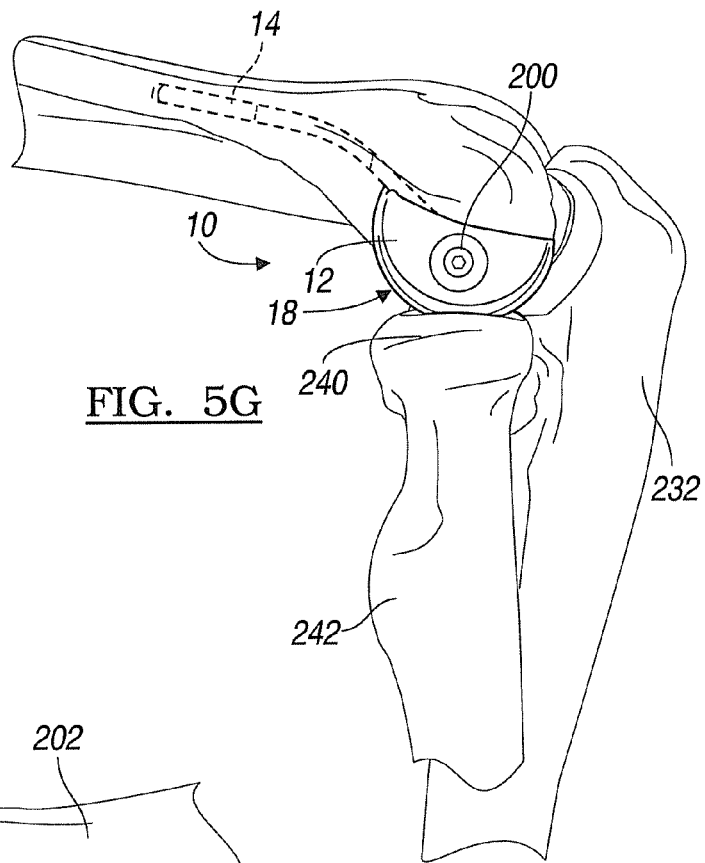
FIG. 5G is a lateral view of the capitellar implant of FIG. 5F shown with the elbow in flexion.
Figure 5H:
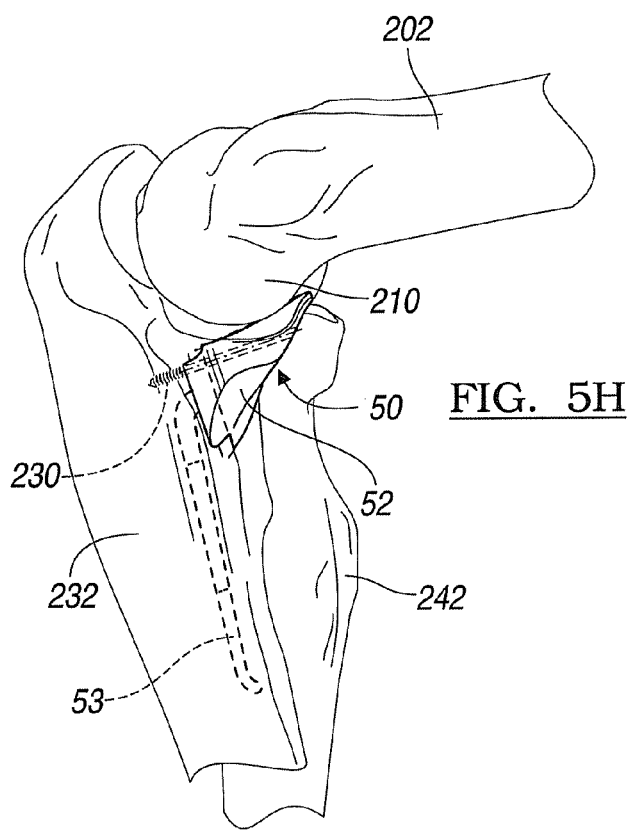
FIG. 5H is a medial view of the coronoid implant of FIGS. 2A-2F shown implanted relative to a host ulna and shown with the elbow in flexion.

The illustrations provided in FIGS. 5E-5H provide additional medial and lateral views of the capitellar and coronoid implants 10 and 50, respectively. More specifically, the coronoid implant 50 is illustrated in the medial view of the elbow joint shown with the humerus 202 and ulna 232 in extension (FIG. 5E). FIG. 5H illustrates the left elbow joint of FIG. 5E shown with the humerus 202 and the ulna 232 in flexion. As shown, the superior articulating surface 64 accommodates rotational engagement of the trochlea 210 during rotation of the humerus 202 and ulna 232. The central ridge 66 and the anterior buttress 68 on the superior articulating surface 64 of the coronoid implant 50 accommodates the geometry of the host trochlea (as best shown in FIG. 5D). The anterior buttress 68 blocks subluxation of the humerus 202 in cases of posterolateral elbow rotary instability.

With specific reference now to FIGS. 5F and 5G, the capitellar implant 10 is shown with the articulating surface 18 slidably communicating along the superior surface of the radial head 240 of the radius 242.

With reference now to FIG. 6A, the capitellar implant 110 is shown with a bone screw 200' adjacent to a humerus 202. An implant engaging surface 205 can be prepared on the distal humerus 202 subsequent to resecting at least portions of a capitellum. A passage 207 can also be prepared that can correspond with alignment to an lateral column of the humerus 202. It is appreciated that the surface 205 and the passage 207 may take other forms than that shown in the example of FIG. 6A. However, it will be appreciated that the capitellar implant 110 can be implanted onto a distal humerus to accommodate coronal shear fractures involving the lateral aspect of the trochlea 210. The capitellar implant 110 can be particularly useful when it is desired to resect additional bone of the lateral trochlear (as compared to the preparation described above with respect to FIG. 5A and receipt of the capitellar implant 10). The bone screw 200' can include a head 212' and a shank 214' having a threaded end 216'. The bone screw 200' can be configured similar to the bone screw 200 described above, however, may have a longer shank 214' to extend further medially into the host trochlea 210 when implanted. In this way, the axial length of the bone screw 200' is greater than the width of the body 116 from the lateral side 130 to the medial side 132 of the articulating head 112, such that at least portions of the threaded end 216' can extend proud from the medial side 132 of the articulating head 112. In one example, the head 212' can provide a geometry substantially complementary to the counterbore 126 provided in the body 116.

Turning now to FIG. 6B, the coronoid implant 150 is shown in exploded view with a bone screw 230 and adjacent to an ulna 232. In the example shown in FIG. 6B, the ulna 232 includes an implant engaging surface 234 where a host coronoid has been resected from the ulna 232. The implant engaging surface 234 can be milled (or cut) to a shape that generally accommodates the wrap-around profile of posterior side 158. A passage 236 can be prepared in the ulna 232. In one example, the passage 236 can correspond with an intramedullary canal of the host ulna. It will be appreciated that the particular geometry of the surface 234 and the passage 236 is merely exemplary and the host ulna 232 may be prepared differently according to the needs of a particular patient.

Figure 6C:
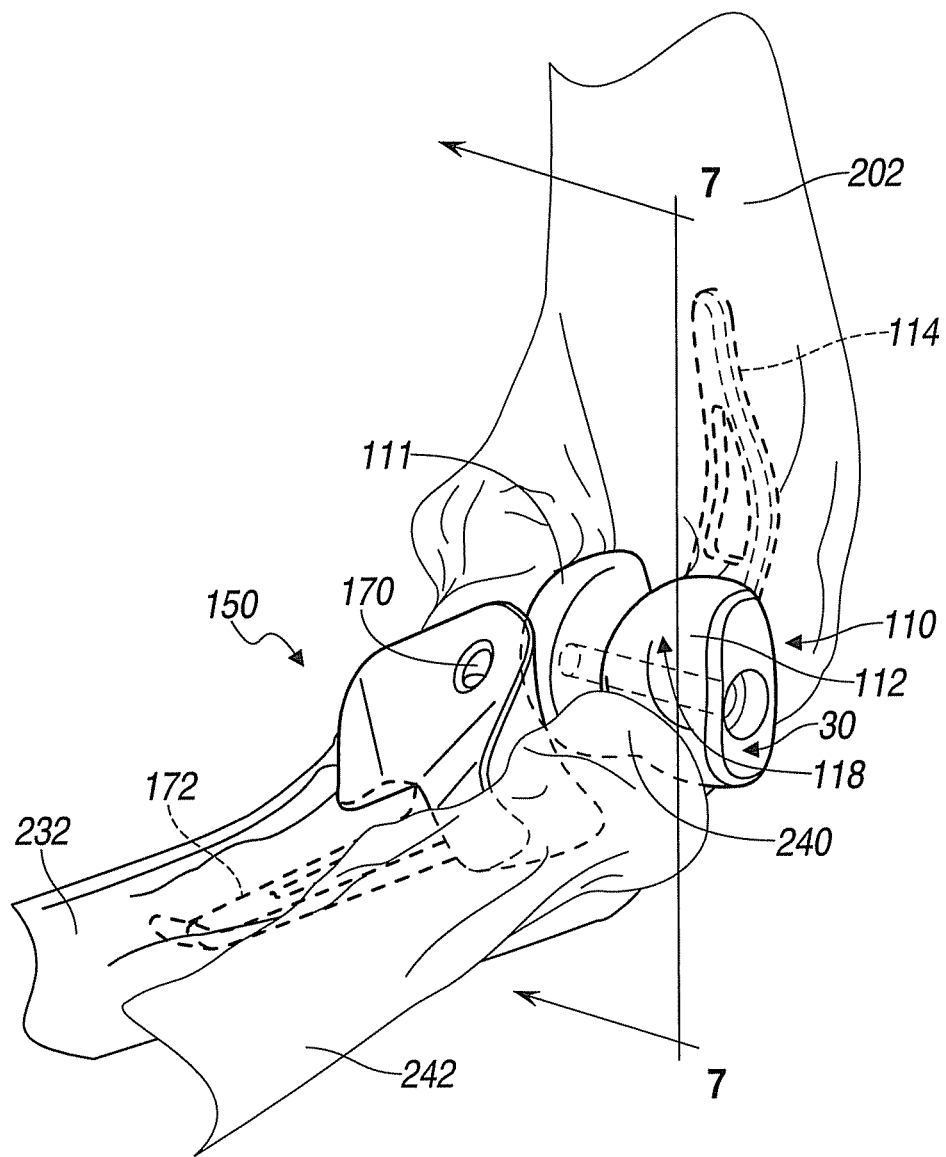
FIG. 6C is a lateral perspective view of a left elbow shown with the capitellar and coronoid implants of FIGS. 3A-4F in an implanted position relative to the host humerus and ulna, respectively, and shown with the elbow in flexion.

Turning now to FIG. 6C, the capitellar implant 112 and the coronoid implant 150 are shown implanted into an exemplary left elbow. For clarity, the bone screw 200' and 230 have been omitted from the illustration in FIG. 6C. As shown, the articulating surface 118 of the articulating body 116 of the capitellar implant 110 can be aligned for articulation with a head 240 of a radius 242. The coronoid implant 150 can be positioned relative to the ulna 232, such that the superior articulating surface 164 is aligned for slidable articulation with the trochlea 210. In the example shown, the articulating surface 164 can be configured with rotation along a portion of the host trochlea 210 and the second articulating surface 119 of the extension portion 111 on the capitellar implant 110.

Figure 6D:
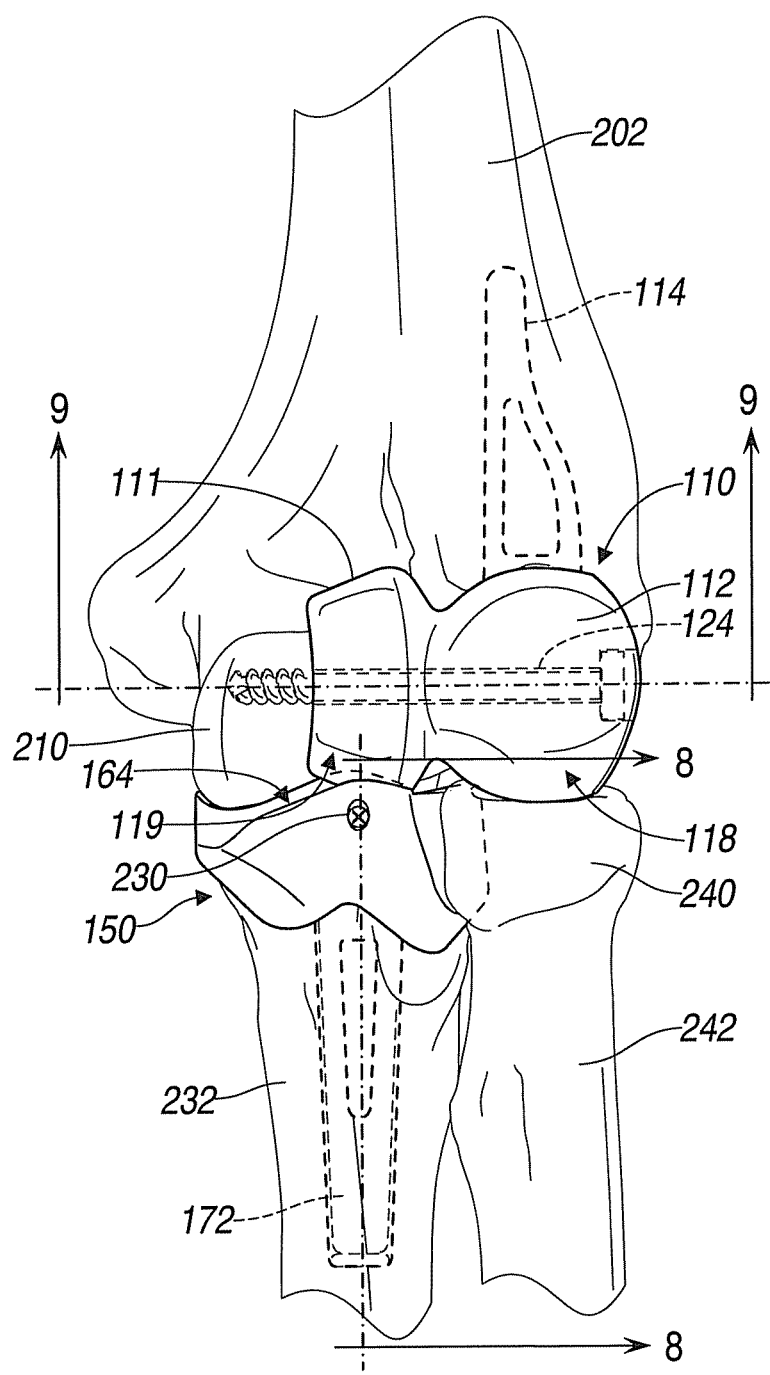
FIG. 6D is an anterior view of the capitellar and coronoid implants of FIGS. 3A-4F shown implanted into a left elbow and shown with the elbow in extension.
Figure 7:
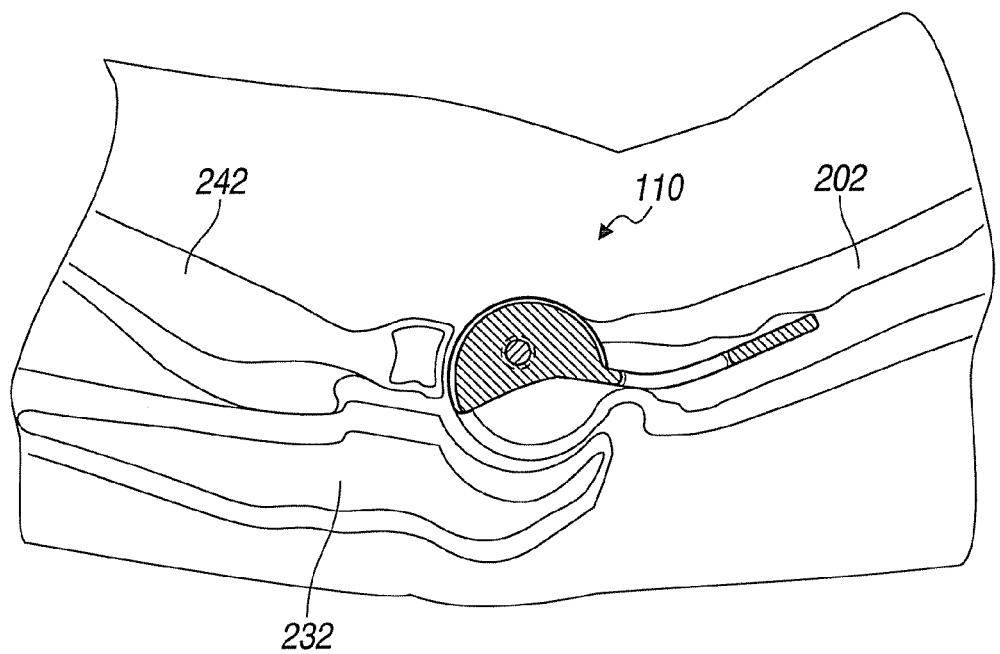
FIG. 7 is a cross-sectional view taken along lines 7-7 of FIG. 6C.
Figure 8:
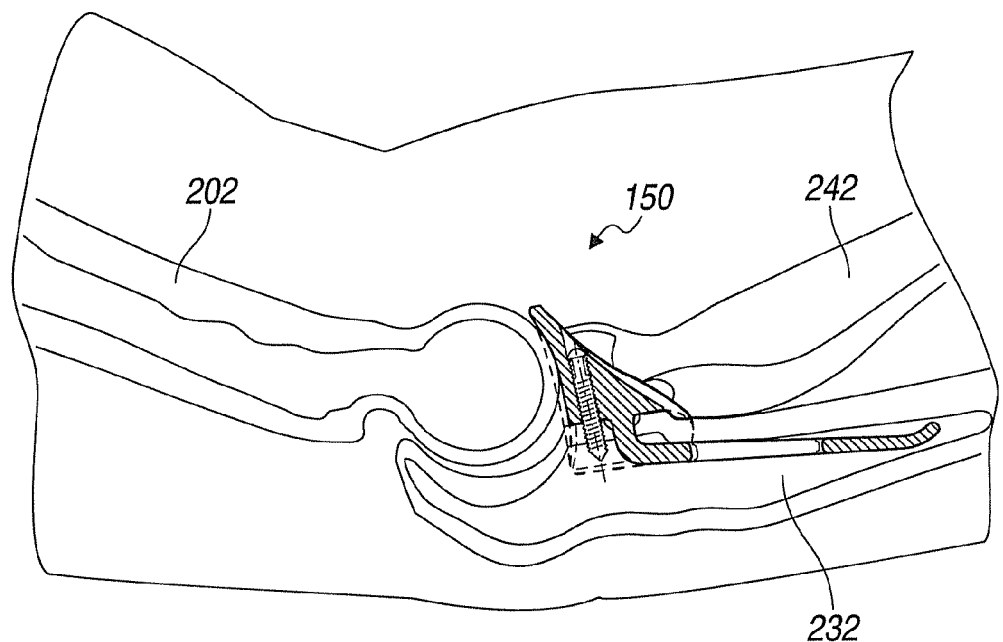
FIG. 8 is a cross-sectional view taken along lines 8-8 of FIG. 6D.
Figure 9:
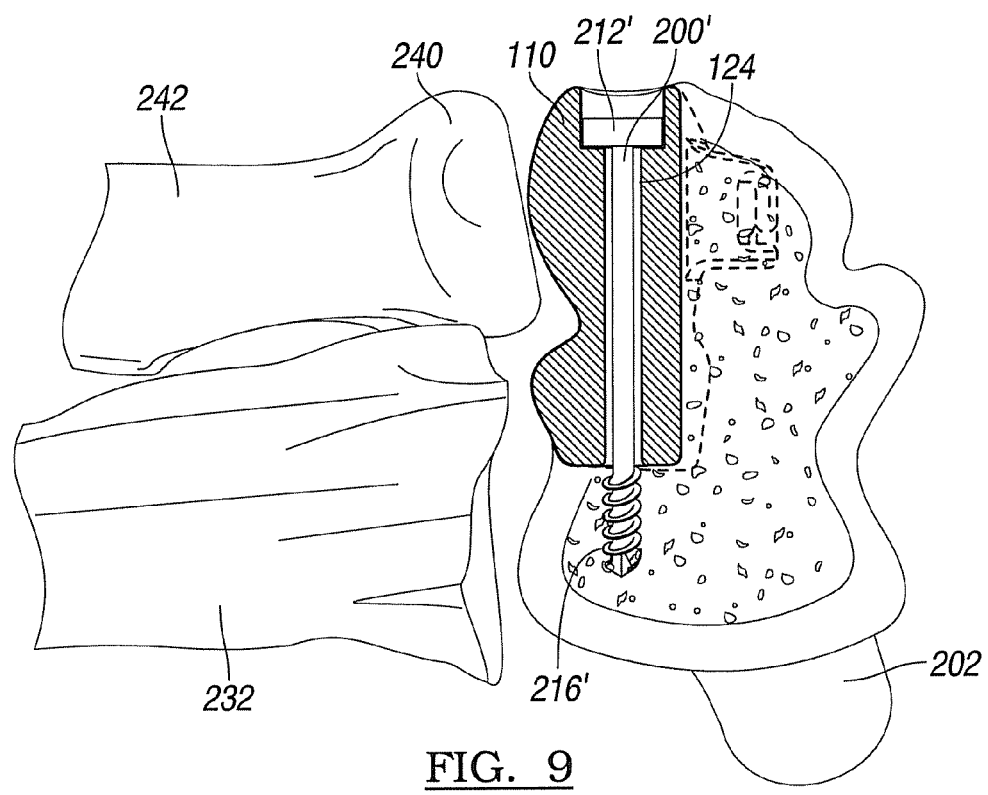
FIG. 9 is a cross-sectional view taken along lines 9-9 of FIG. 6D.
Figure 10:
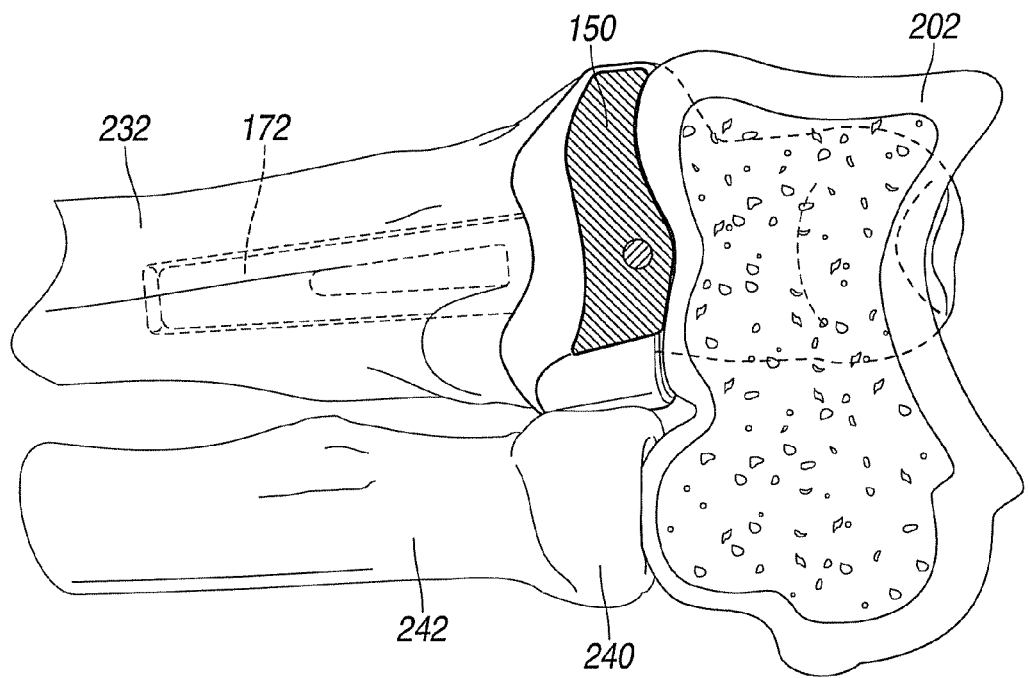
FIG. 10 is a cross-sectional view taken along lines 10-10 of FIG. 6E.
Figure 12:
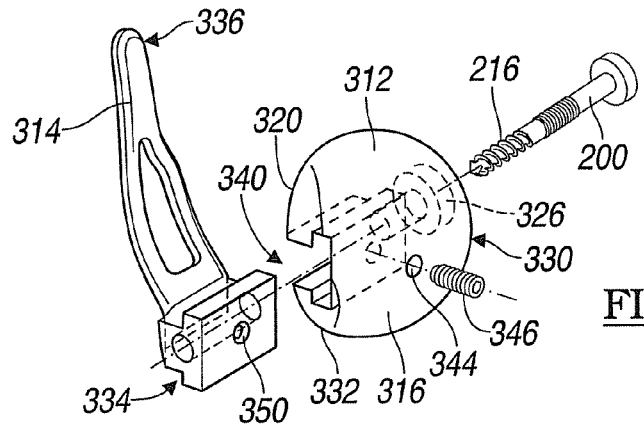
FIG. 12 is a medial perspective exploded view of a modular capitellar implant according to various features of the present teaching.
Figure 13:
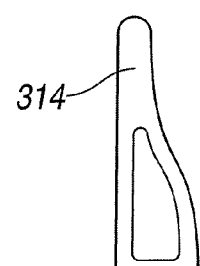
FIG. 13 is a cross-sectional view of the modular capitellar implant of FIG. 12 and taken along the axis of the fastener.
Figure 14:
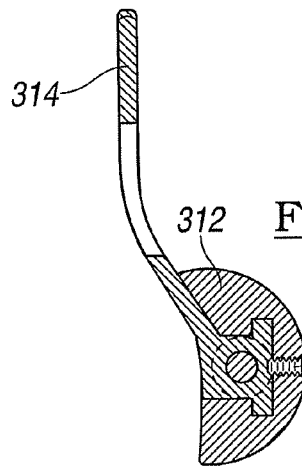
FIG. 14 is a cross-sectional view of the modular capitellar implant of FIG. 12 and taken along a plane perpendicular to an axis of the fastener.

As shown in FIG. 6D, the capitellar implant 110 and the coronoid implant 150 are illustrated in an implanted position relative to a left elbow in extension. Notably, the bone screw 200' has been passed through the passage 124 from a lateral to a medial direction, such that the threaded end 216' threadably advances into the trochlea 210. The bone screw 200' therefore can provide additional fixation of the capitellar implant 110 relative to the host humerus 202 in addition to the fixation properties provided by the stem 114. Furthermore, the bone screw 230 is shown advanced through the passage 170 provided in the articulating portion 152 of the coronoid implant 150. The bone screw 230 can threadably advance into the host ulna 232 in a direction that is substantially perpendicular to a long axis of the stem 172. The bone screw 230 can provide supplemental fixation of the coronoid implant 150 relative to the ulna 232 in addition to the stem 172.

The illustrations provided in FIGS. 6E and 6F provide additional medial and lateral views of the coronoid and capitellar implants 150 and 10, respectively. More specifically, the coronoid implant 150 is illustrated in the medial view of the elbow joint shown with the humerus 202 and ulna 232 in extension (FIG. 6E). FIG. 6F shows the capitellar implant in the lateral view of the elbow joint shown with the humerus 202 and the ulna 232 in extension. The central ridge 166 and the anterior buttress 168 on the superior articulating surface 164 of the coronoid implant 150 accommodates the geometry of the host trochlea 210 (as best shown in FIG. 6D). The anterior buttress 168 blocks subluxation of the humerus 202 in cases of posterolateral elbow rotary instability. The cross-sectional views of FIGS. 7-10 provide additional views of the various capitellar and coronoid implants 110 and 150 in an implanted position.

Turning now to FIGS. 11A-11C, the capitellar implant 112 and the coronoid implant 150 are shown implanted into a host humerus 202 and ulna 232, respectively. The coronoid implant 150 is shown cooperating with an exemplary radial implant 250 that is shown implanted into the host radius 242. Additional features of the radial implant 250 can be found in commonly owned U.S. Pat. No. 6,656,225, which is expressly incorporated herein by reference. In this way, the articulating surface 118 of the articulating head 112 can slidably communicate along an opposing surface of the radial implant 250. In addition, according to some examples, the radial articulating surface 165 of the coronoid implant 150 can communicate with the radial implant 250. It will be appreciated that the radial implant 250 is merely exemplary and other radial implants may be provided for cooperating with either or both of the capitellar implant 110 and coronoid implant 150.

Figure 15:
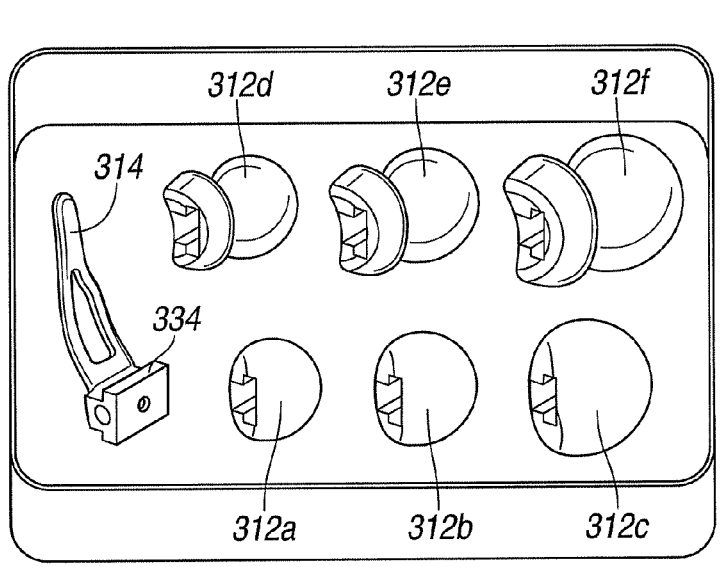
FIG. 15 is a perspective view of an exemplary kit having a plurality of modular articulating heads that each couple with a stem according to various features of the present teachings.

With reference now to FIGS. 12-15, a capitellar implant 310 constructed in accordance to additional features of the present teachings will be described. The capitellar implant 310 generally comprises a modular articulating head 312 and a stem 314. The articulating head 312 can include an articulating body 316 and a humeral engaging surface 320. A passage 324 having a counterbore 326 can be formed through the articulating body 316 from a lateral side 330 to a medial side 332. The articulating body 316 of the articulating head 312 can be modular and can be provided as part of a kit 333 (FIG. 15). As can be appreciated, a plurality of modular articulating heads (along with different size stems) 312A-312F can be provided that have various geometries, such that a surgeon can select an appropriate match based upon any given patient's particular needs.

The stem 314 can generally extend from a connecting end having a first interlocking portion 334 to a distal end 336. The articulating head 312 can include a second interlocking portion that is configured to selectively receive the first interlocking portion 334 of the stem 314. In the examples shown, the first interlocking portion is in the form of a T-shaped male insertion portion and the second interlocking portion is the form of a T-shaped female receiving portion. The articulating head 312 is configured to be slidably received onto the T-shaped male insertion portion 334 from a lateral to a medial direction. In some examples, it may be desirable to connect the articulating head 312 to the stem 314 intraoperatively, such as during trialing or when it may be desirable to change an articulating head 312 without having to disturb an already implanted stem 314. The articulating head 312 can further define an opening 344 that receives a set screw 346 for further securing the articulating head 312 to a recess 350 provided on the first interlocking portion 334. In one example, articulating head 312 can be solely secured by the lock screw 200 (FIG. 13) that threads into the T-shaped male insertion of the stem and also into the medial trochlear. In another example, the articulating head 312 can be secured solely by the set screw 346. In other examples, the articulating head 312 can be secured by a combination of both the lock screw 200 and the set screw 346.

While the examples shown illustrate the male insertion portion being formed on the stem 314 and the female receiving portion being formed on the articulating head 312, these features may be swapped. Furthermore, while the specific geometries illustrated as a T-shaped section, other geometrical configurations may be provided.

Figure 16:
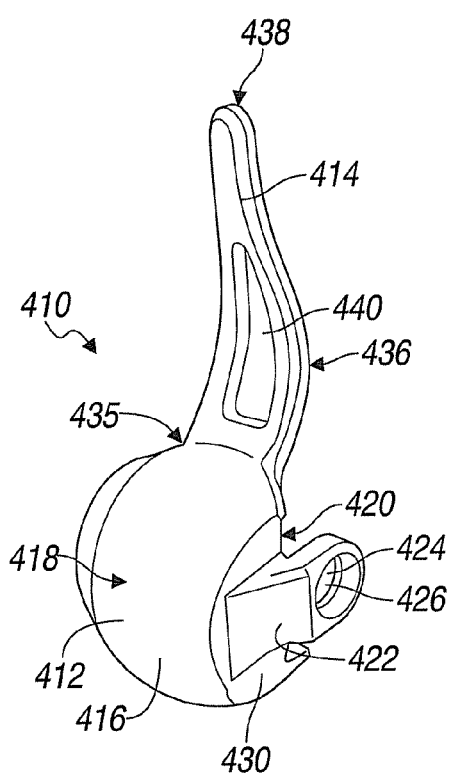
FIG. 16 is a perspective lateral view of a capitellar implant constructed in accordance with additional features of the present teachings.
Figure 17:
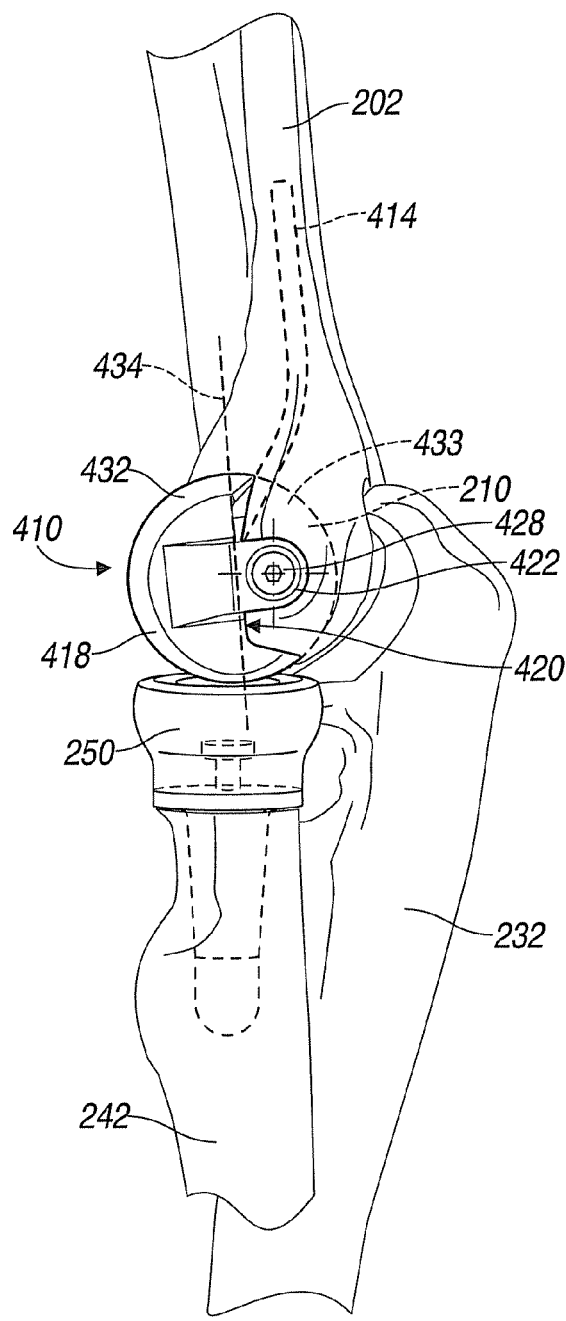
FIG. 17 is a lateral view of a left elbow in extension and shown with the capitellar implant of FIG. 16 in an implanted position relative to a distal humerus.

With reference now to FIGS. 16 and 17, a capitellar implant 410 constructed in accordance to one example of the present teachings will be described. In general, the capitellar implant 410 can be implanted at the distal humerus (FIG. 17) in circumstances where it may be desirable to accommodate fracture patterns along the articulating surfaces or other deformities observed about the distal humerus articular surface. The capitellar implant 410 can generally comprise an articulating head 412 and a stem 414. The capitellar implant 410 in the examples shown in FIGS. 16 and 17 is a unitary or monolithic component.

The articulating head 412 can include an articulating body 416 having an arcuate articulating surface 418 and a humeral engaging surface 420. The articulating body 416 can further comprise a posteriorly extending attachment lobe 422. The attachment lobe 422 can have a passage 424 and a counterbore 426 formed therein. In general, the attachment lobe 422 can be formed on a lateral side 430. As will be described, the passage 424 can be operable to receive a bone screw 428 (FIG. 17) during implantation.

As best illustrated in FIG. 17, the articulating surface 418 can be generally hemispherical around the articulating body 416. The humeral engaging surface 420 can generally be concave, such that the articulating surface 418 can be provided around an area greater than 180° of the articulating body 416. In some examples, the concave humeral engaging surface 420 can facilitate nesting of a prepared distal humerus. According to one geometrical relationship of the capitellar implant 410 shown in FIGS. 16 and 17, the articulating body 416 can generally have a first substantially hemispherical portion 432 and a second portion 433 separated by an equatorial plane 434. According to one advantage of the capitellar implant 410, a majority of the articulating surface 418 is provided on the first substantially hemispherical portion 432, whereas the attachment lobe 422 extends posteriorly on the opposite side and spaced away from the equatorial plane 434, such that the passage 424 is located generally in an area to align more posteriorly into the trochlea 210 of the humerus 202. As can be appreciated, with the bone screw 428 located posteriorly (into the second portion 433), a more substantial portion of the trochlear 210 can be utilized for attaching the bone screw 428.

The humeral engaging surface 420 can be porous coated or roughened to further encourage bony ingrowth. The anterior profile of the articulating body 416 can generally be circular and have a truncated lateral side 430. The articulating body 416 can be provided on the capitellar implant 410 having a geometry that substantially replicates at least portions of a natural capitellum of the patient. In this regard, a plurality of capitellar implants 410 can be provided having articulating heads 414 with various geometries, such that a surgeon can select an appropriate match, based upon a patient's particular needs or fracture areas.

The stem 414 can generally extend from a connecting end 435 that is attached to the articulating body 416 through a curved intermediate portion 436 to a proximal end 438. The generally planar body 416 can promote rotational stability. The stem 414 can define an opening 440 that can facilitate bone ingrowth when implanted into a prepared lateral column of a humerus. The opening 440 can have a generally triangular profile. In some examples, the opening 440 can be used to receive one or more bone screws for securably positioning the stem 414 relative to a humerus. While the particular examples shown in FIG. 17 shows the stem 414 implanted into a prepared lateral column of the humerus 202, the capitellar implant 410 can additionally or alternatively be positioned on an anterior face of the humerus 202. In one example, the stem 414 and/or the articulating head 412 can be formed of biocompatible materials, such as, but not limited to, any combinations of titanium, cobalt, polyethylene, pyrocarbon, PEEK, including carbon fiber reinforced PEEK, or other materials. As shown in FIG. 17, the capitellar implant 410 can be configured to cooperate with the exemplary radial implant 250 that is shown implanted into the host radius 242.

Figure 18:
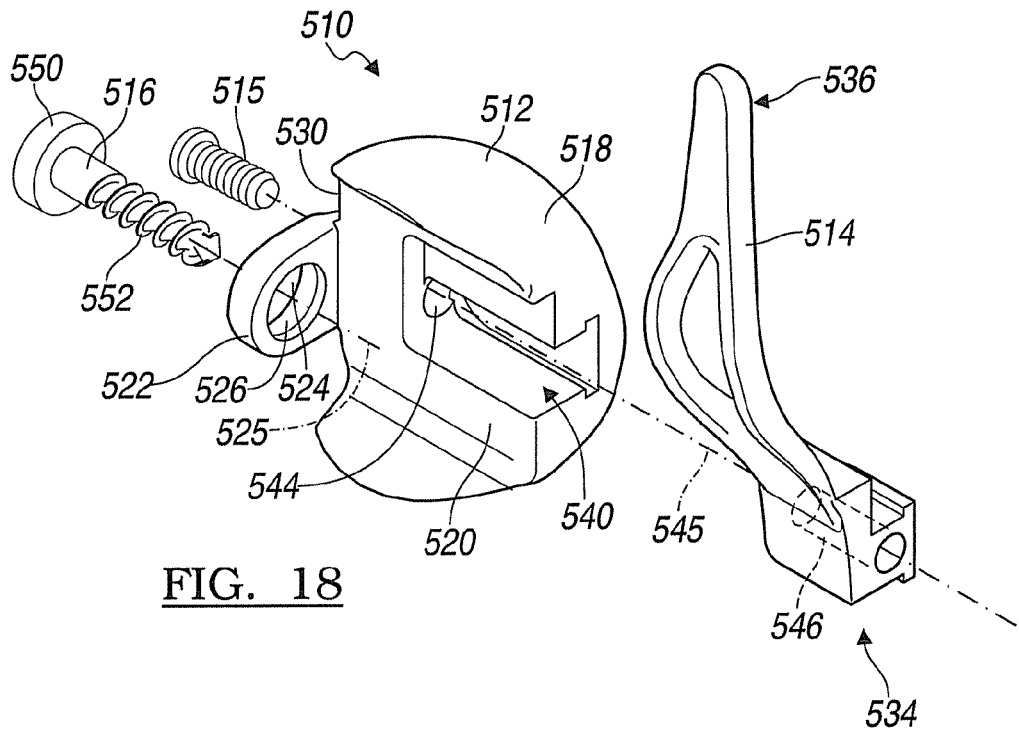
FIG. 18 is a medial perspective exploded view of a modular capitellar implant according to various features of the present teachings.
Figure 19:
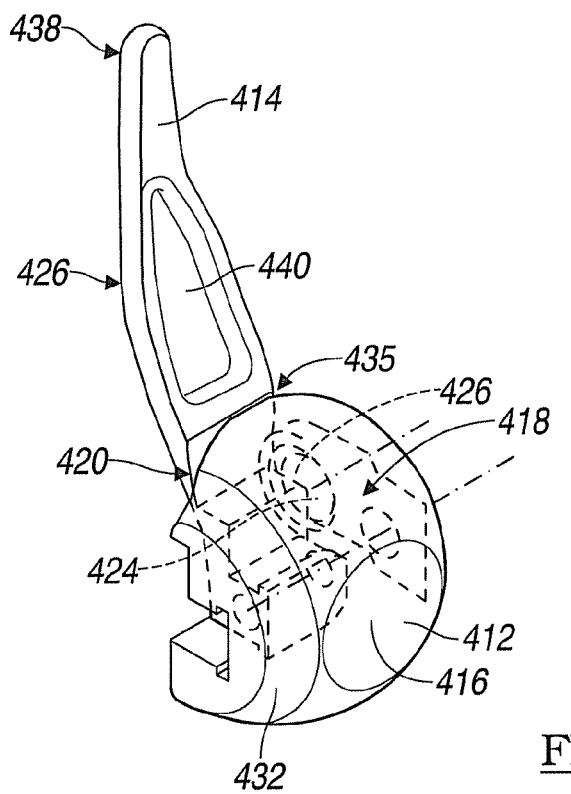
FIG. 19 is a medial perspective view of the modular capitellar head and modular stem of FIG. 18.
Figure 20:
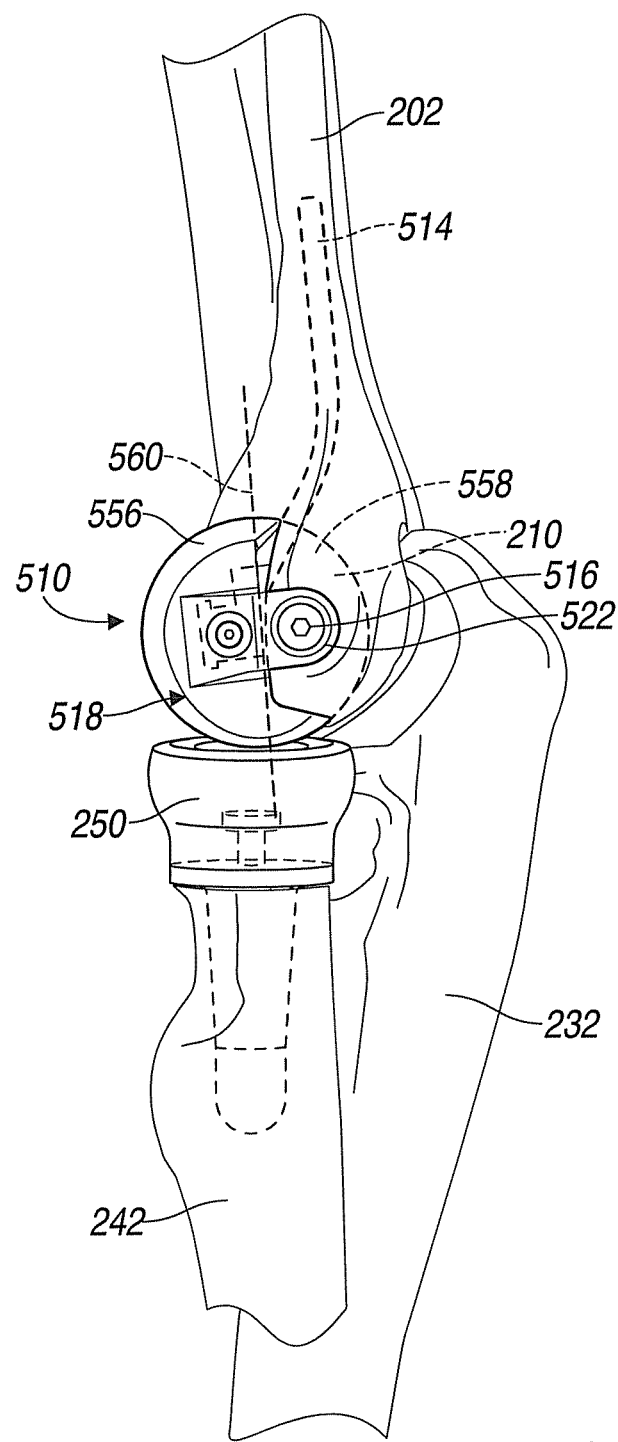
FIG. 20 is a lateral view of the capitellar implant of FIG. 18 and shown implanted into a left elbow in extension.

With particular reference now to FIGS. 18 and 19, a capitellar implant 510 constructed in accordance to additional features of the present teachings will be described. The capitellar implant 510 can generally comprise a modular articulating head 512, a stem 514, a first securing member 515 and a second securing member 516. The first securing member 515 can be used to generally connect the articulating head 512 to the stem 514 as will be described. The second securing member 516 can generally comprise a bone screw that can be used to connect the articulating head 512 to the host humerus. The articulating head 512 can generally include an articulating body 518 and a humeral engaging surface 520. The articulating body 518 can further comprise an attachment lobe 522 extending generally posteriorly therefrom. The attachment lobe 522 can generally include a passage 524 extending along an axis 525 and a counterbore 526. The attachment lobe 522 can generally be formed on a lateral side 530 of the modular articulating head 512. The articulating body 518 of the modular articulating head 512 can be modular and can be provided as part of a kit, such as shown in FIG. 15. As can be appreciated, a plurality of modular articulating heads (along with different sized stems), can be provided that have various geometries, such that a surgeon can select an appropriate match based upon any given patient's particular needs.

The stem 514 can generally extend from a connecting end having a first interlocking portion 534 to a proximal end 536. The articulating head 512 can include a second interlocking portion 540 that can be configured to selectively or slidably receive the first interlocking portion 534 of the stem 514 to rotationally key the articulating head 512 to the stem 514. In the examples shown, the first interlocking portion 534 is in the form of a T-shaped male insertion portion and the second interlocking portion is in the form of a T-shaped female receiving portion. The articulating head 512 can be configured to be slidably received onto the T-shaped male insertion portion 534 from a lateral to a medial direction. In some examples, it may be desirable to connect the articulating head 512 to the stem 514 intraoperatively, such as during trialing or when it may be desirable to change an articulating head 512 without having to disturb an already implanted stem 514.

The articulating head 512 can further define an opening 544 that extends along an axis 545. The axes 525 and 545 can be parallel. The opening 544 can be configured to receive the first securing member 515 that can threadably mate into a threaded passage 546 defined in the stem 514. The second securing member 516 can generally include a head portion 550 and a threaded shank portion 552. The head portion 550 can be configured to suitably nest within the counterbore 526 of the attachment lobe 522.

Similar to the capitellar implant 410 described above with respect to FIGS. 16 and 17, the capitellar implant 510 can have favorable geometrical characteristics that can facilitate more stabile connection to the trochlea 210. Explained further, the articulating body 518 can generally have a first hemispherical portion 556 and a second portion 558 separated by an equatorial plane 560. A majority of the articulating body 518 can be provided on the first hemispherical portion 556 whereas the attachment lobe 522 can extend further posteriorly into the second portion 558. In this regard, the second securing member 516 can also extend into the second portion 558 for threadably advancing into a substantial portion of the trochlea 210.

Figure 21A:
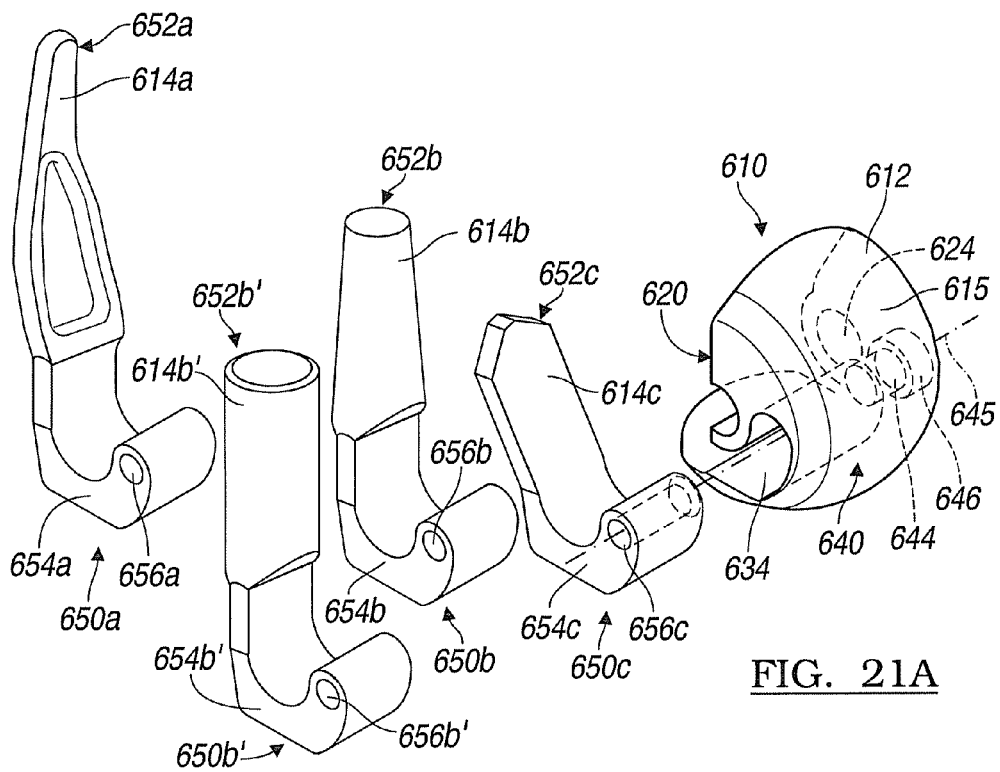
FIG. 21A is a medial perspective exploded view of a capitellar implant shown with a series of modular capitellar stems that are selectively and intraoperatively connectable to the capitellar head.
Figure 21B:
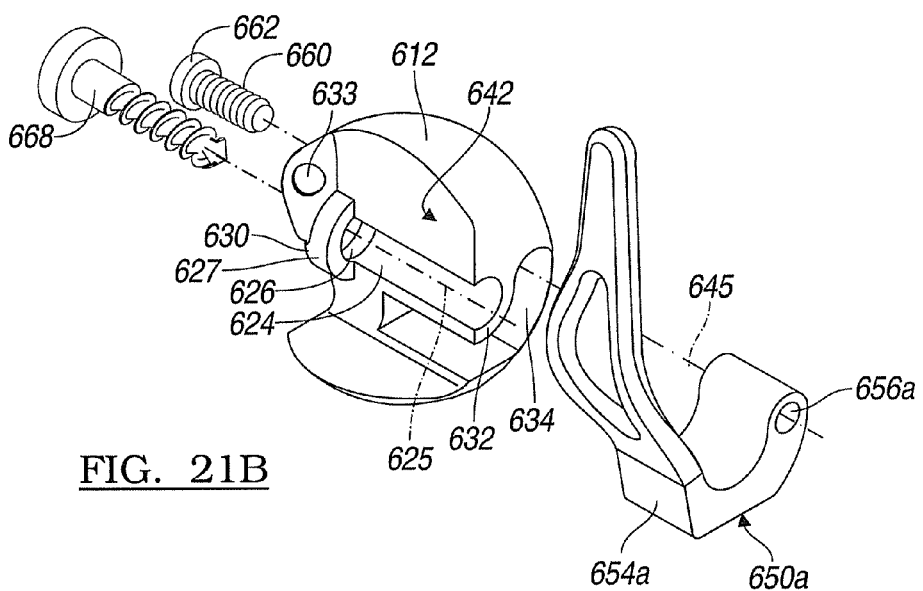
FIG. 21B is a medial exploded view of the modular capitellar head and large stem shown in FIG. 21A and further illustrated with a first connection member that connects the modular stem with the capitellar head and a second connection member that cooperates with the capitellar head and is configured to be further threadably engaged into the trochlea.

With reference now to FIGS. 21A and 21B, a capitellar implant 610 constructed in accordance to additional features of the present teachings will be described. The capitellar implant 610 generally comprises a modular articulating head 612 and a plurality of stems 614a, 614b, 614b' and 614c. The stems 614a, 614b, 614b' and 614c can be porous coated. As will become appreciated from the following discussion, the articulating head 612 can be configured to selectively and intraoperatively connect with any of the stems 614a, 614b, 614b' or 614c according to the needs of a given patient. The articulating head 612 can generally include an articulating body 616 and a humeral engaging surface 620. The articulating body 616 can generally have a first substantially hemispherical portion 621 and a second portion 622 separated by an equatorial plane 623. A central passage 624 extending along an axis 625 and having a counterbore 626 can be formed through an attachment lobe 627 of the articulating body 616 from a lateral side 630 to a medial side 632. The passage 624 is formed at the equatorial plane so that a portion of the passage 624 is on a side of the equatorial plane 623 opposite the hemispherical portion 621. An auxiliary passage 633 can be formed in the articulating head 612. An auxiliary bone screw can be passed through the auxiliary passage 633 and into the trochlear 210. The auxiliary passage 633 can be used to drive a supplemental fastener into bone at a non-parallel orientation with respect to the first securing member 660. The supplemental fastener can take advantage of additional bone to complement the securing force of the first securing member 660. The articulating body 616 can further include a receiving groove 634 formed therein. The articulating body 616 can also include an articulating surface 640 and a humeral engaging surface 642. An offset passage 644 extending along an axis 645 can be formed in the articulating body 616. The axes 625 and 645 can be parallel. The offset passage 644 can define a counterbore 646.

Figure 25:
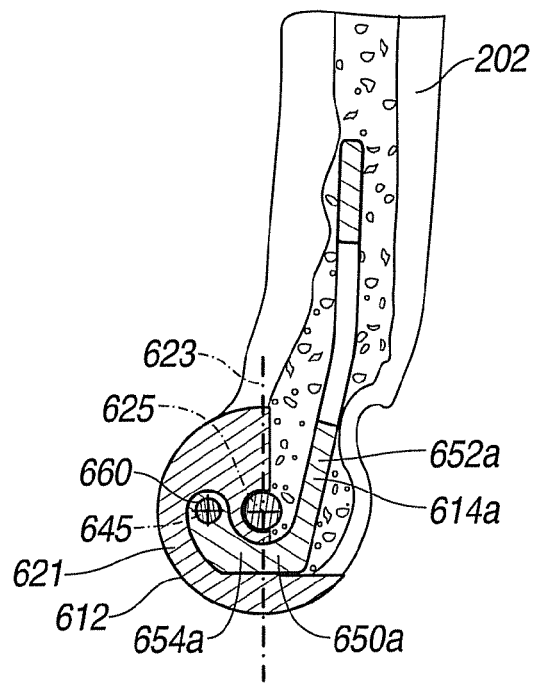
FIG. 25 is a sectional view taken along lines 25-25 of FIG. 24.

Each of the stems 614a, 614b, 614b' and 614c can generally comprise a connecting end 650a, 650b, 650b' and 650c and a proximal end 652a, 652b, 652b' and 652c. The proximal end 652a can be generally planar with an aperture formed therein. The proximal end 652b can be generally in the form of a tapered cylinder. The proximal end 652b' can be generally in the form of a straight cylinder. The proximal end 652c can be generally planar and have a shorter length as compared to the other proximal ends 652a and 652b. The connecting ends 650a, 650b and 650c can each provide a generally curved body 654a, 654b and 654c that have a geometrical profile that substantially matches the receiving groove 634. Bores 656a, 656b and 656c are provided in the respective curved body 654a, 654b and 654c. The bores 656a, 656b and 656c are configured to be coaxial with the axis 645 in the assembled position (FIG. 25).

While the following discussion is specifically directed toward use with the stem 614a, those skilled in the art will readily appreciate that either of the other stems 614b or 614c can alternatively be used. As can be appreciated, the curved body 654a of the stem 614a can be slidably inserted into the receiving groove 634 of the articulating body 616. The bore 656a is axially aligned with the offset passage 644. In this regard, a first securing member 660 can be advanced into the offset passage 644 to threadably engage the threaded bore 656a of the stem 614a. In some examples, the first securing member 660 can further include a head 662 that nests into the counterbore 646 on the articulating body 616. Notably, with the "J-shaped" profile of the connecting end 650a of the stem 614a, the stem 614a can be suitably connected to a substantial portion of the articulating body 616 without interfering with the central passage 624 that is dedicated for receipt of a second securing member 668 that is configured to threadably engage the trochlea 210 of the humerus 202.

Figure 22:
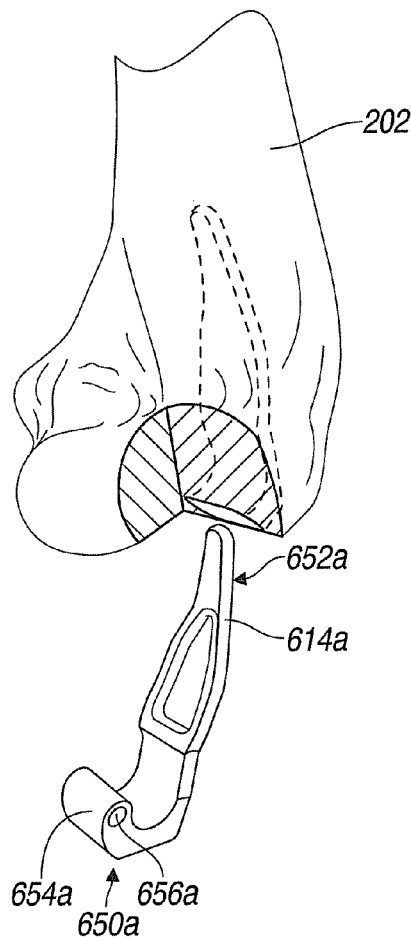
FIG. 22 is a lateral perspective view of a distal humerus and shown with a modular stem being inserted into a passage prepared in the distal humerus.
Figure 23:
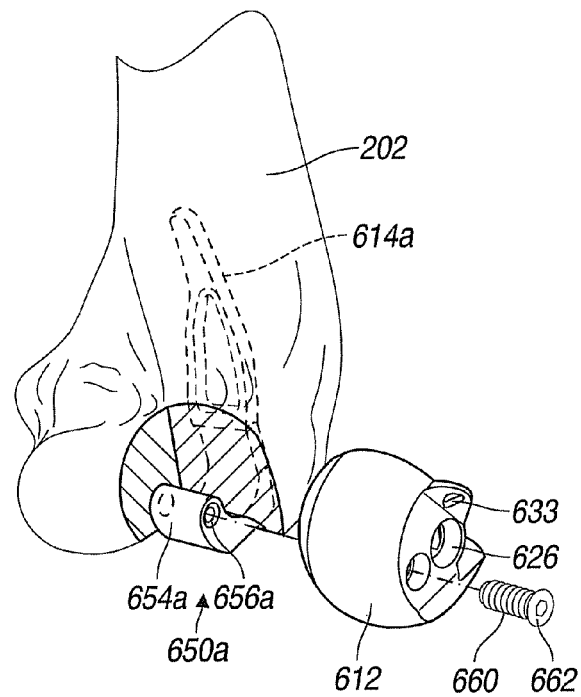
FIG. 23 is a lateral perspective view of the distal humerus of FIG. 22 and shown with the modular capitellar head being initially connected to the stem with the first connection member.

With reference to FIGS. 22 and 23, an exemplary method of implanting the stem 614a and articulating head 612 is shown. At the outset, an implant engaging surface 204 can be prepared on the distal humerus 202 subsequent to resecting at least portions of a capitellum. In some examples, the implant engaging surface 204 can be milled or cut in a planar shape that corresponds to the humeral engaging surface 620. A passage 206 can then be prepared that can correspond with alignment to an lateral column of the humerus 202. The proximal end 652a of the stem 614a can then be inserted into the passage 206. The first securing member 660 can then be located into the offset passage 644 of the articulating head 612 while the curved body 654a of the stem 614a is located into the receiving groove 634 of the articulating head 612. The first securing member 660 can then be threaded into the bore 656a of the stem 614a connecting the articulating head 612 to the stem 614a. The second securing member 668 can then be located through the central passage 624 and into the distal humerus 202.

Figure 24:
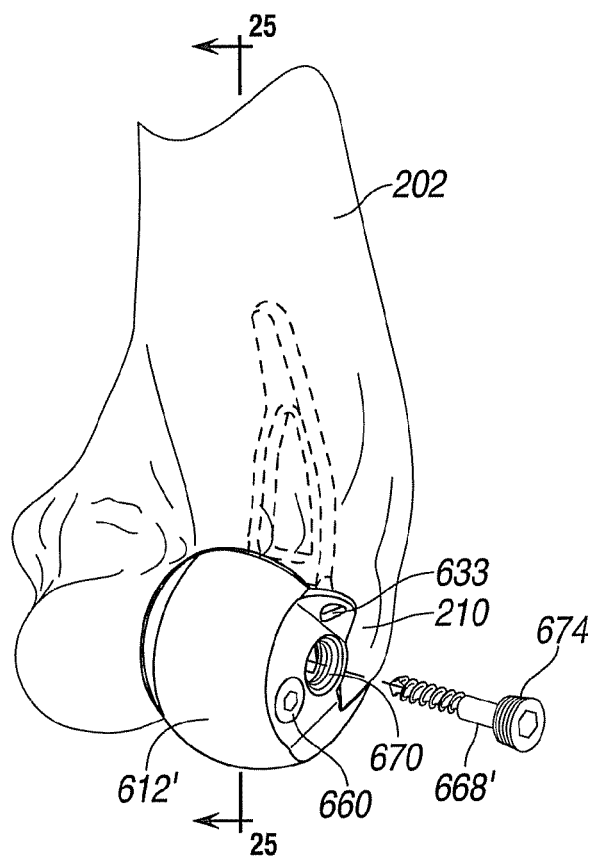
FIG. 24 is a lateral perspective view of the distal humerus of FIG. 23 and shown with a second connection member being subsequently passed into the capitellar implant for threadable engagement into the trochlear.

According to another embodiment shown in FIG. 24, an articulating head 612' can have a threaded portion 670 that can mate with threads 674 formed on bone screw 668'. The bone screw 668' is a locking screw and can be incorporated for use with any of the other capitellar implants disclosed herein. Accordingly, in some embodiments, such capitellar implants may define a threaded bore for mating with the threads 674 on the bone screw 668'. It will further be appreciated that the configurations of the capitellar implants 410, 510 and 610 can be implanted for use with any of the other implants disclosed herein such as the coronoid implants 50 and 150. Moreover, any of the capitellar implants 410, 510 and 610 can be configured to additionally include a pair of bulbous portions such as shown on the capitellar implant 110 (FIGS. 3A and 3E).

While the description in the specification and illustrated in the drawings are directed to various embodiments, it will be understood that various changes may be made and equivalents may be substituted for elements thereof without departing from the scope of the teachings and the appended claims. In addition, many modifications may be made to adapt a particular situation or material to the teachings without departing from the scope thereof. Therefore, it is intended that the teachings and claims are not be limited to any particular embodiment illustrated in the drawings and described in the specification, but that the teachings and claims can include any embodiments falling within the foregoing description and the appended claims.

What is claimed is:

1. An elbow prosthesis comprising:
a capitellar implant including a modular articulating head and a stem, the articulating head adapted to be selectively coupled to the stem and having a first substantially hemispherical portion and a second portion that collectively extend between lateral and medial sides of the articulating head and separated by a plane, the first substantially hemispherical portion having an articulating surface generally between the lateral and medial sides that is configured to articulate with one of a radial implant or and a natural radius, and the second portion having an attachment lobe extending on the lateral side and that defines a passage therethrough, the passage extending at least partially in the second portion,
wherein the stem includes a first interlocking geometry formed at the connecting end and the articulating head includes a second interlocking geometry, the first interlocking geometry includes one of a J-shaped male insertion portion and a J-shaped female receiving portion and the second interlocking geometry includes the other of the male and female receiving portions, wherein the J-shaped female receiving portion slidably receives the J-shaped male insertion portion in an assembled position.

2. An elbow prosthesis comprising:
a capitellar implant including a modular articulating head and a stem, the articulating head adapted to selectively coupled to the stem and having a first substantially hemispherical portion and a second portion that collectively extend between lateral and medial sides of the articulating head and separated by a plane, the first substantially hemispherical portion having an articulating surface generally between the lateral and medial sides that is configured to articulate with one of a radial implant or and a natural radius, and the second portion having an attachment lobe extending on the lateral side and that defines a passage therethrough, the passage extending at least partially in the second portion,
wherein the stem includes a first interlocking geometry formed at the connecting end including one of a T-shaped male insertion portion and a T-shaped female receiving portion, and the articulating head includes a second interlocking geometry having the other of the male and female receiving portions, wherein the T-shaped female receiving portion slidably receives the T-shaped male insertion portion in an assembled position, wherein a throughbore is defined through the first and second interlocking geometries that accommodates a securing member in an implanted position, wherein the throughbore is defined exclusively on the first substantially hemispherical portion.

3. An elbow prosthesis comprising:
a capitellar implant including an articulating head and a stem, the articulating head having a first substantially hemispherical portion and a second portion that collectively extend between lateral and medial sides of the articulating head and separated by a plane, the first substantially hemispherical portion having an articulating surface generally between the lateral and medial sides that is configured to articulate with one of a radial implant or and a natural radius, and the second portion having an attachment lobe extending on the lateral side and that defines a passage therethrough, the passage extending at least partially in the second portion, wherein the articulating head and stem are monolithic.

4. The elbow prosthesis of claim 3 wherein the stem is porous coated.

* * * * *